(12) United States Patent
Tribelski

(10) Patent No.: US 6,468,433 B1
(45) Date of Patent: Oct. 22, 2002

(54) METHOD FOR DISINFECTING LIQUIDS AND GASES AND DEVICES FOR USE THEREOF

(76) Inventor: Zamir Tribelski, Derech Haachayor 9, Ein Karem, 95744, Jerusalem (IL)

( * ) Notice: Subject to any disclaimer, the term of this patent is extended or adjusted under 35 U.S.C. 154(b) by 0 days.

(21) Appl. No.: 09/555,126
(22) PCT Filed: Dec. 1, 1998
(86) PCT No.: PCT/IL98/00589
§ 371 (c)(1), (2), (4) Date: Jul. 20, 2000
(87) PCT Pub. No.: WO99/27970
PCT Pub. Date: Jun. 10, 1999

(30) Foreign Application Priority Data

Dec. 1, 1997 (IL) ............................................... 122388

(51) Int. Cl.[7] ................................................... C02F 1/30
(52) U.S. Cl. .................. 210/748; 205/432 R; 205/435; 422/4; 422/22
(58) Field of Search ...................... 210/748; 250/432 R, 250/435; 422/4, 22

(56) References Cited

U.S. PATENT DOCUMENTS 4,376,637 A * 3/1983 Yang 5,262,066 A * 11/1993 Van Soye et al.
5,821,175 A * 10/1998 Engelsberg

FOREIGN PATENT DOCUMENTS

| WO | 92 18170 | 10/1992 |
|----|----------|---------|
| WO | 95 13098 | 5/1995 |
| WO | 96 04935 | 2/1996 |

OTHER PUBLICATIONS

Patent Abstract of JP 63 302940.
Patent Abstract of JP 04 033659.
Patent Abstract of JP 61 111189.
Patent Abstract of JP 08 238476.

* cited by examiner

Primary Examiner—Betsey Morrison Hoey
(74) Attorney, Agent, or Firm—Lowe Hauptman Gilman & Berner, LLP

(57) ABSTRACT

A method for disinfecting liquids and gases includes the steps of distributing at least one optical fiber in the region containing the liquids or gases to be disinfected; aligning at least one radiation unit having a high intensity source of light into said fibers; radiating the liquid or gases by the optical fiber over a predetermined period of time. The present invention further related to devices using the same method.

47 Claims, 13 Drawing Sheets

METHOD FOR DISINFECTING LIQUIDS AND GASES AND DEVICES FOR USE THEREOF

FIELD OF THE INVENTION

The present invention relates to a novel method for disinfecting liquids and gases and to devices using this method. More specifically, the present invention relates to a methods for disinfecting liquids and gasses by light which is radiated into the liquids and gasses by optical fibers. The light may be ultra violet light (UVA, UVB, UVC) which is especially useful for killing bacteria or microscopic noxious microorganism (such as those passing through filtration units). The light may be also in the visible region of the spectrum, which is especially useful for disturbing the breeding cycle of cockroaches (such as those living in sewage networks or other close spaces). Alternatively, the light may be in any other spectral range suitable for killing noxious microorganisms.

(Example: Optical fibers terminated into a modular crystal interface, such as a KTP and/or an LBO, and/or PPKTP and/or other appropriately phase matched or coupled crystals for harmonic generation or frequency doubling for the purpose of disinfecting liquids and gasses) the light is primarily in the IR, NIR, or VISIBLE regions of the spectrum while in delivery and converted to Ultra violet or 2nd, or 3rd, or 4th harmonic generation (UVA, UVB, and UVC).

BACKGROUND OF THE INVENTION

Radiation is known to effect many species population factors in natural, industrial, and domestic ecological systems. The term "radiation" in the context of the present invention includes all the spectral ranges including the visible spectrum i.e. illumination. Radiation of one frequency may effect an increase in the population of one species while simultaneously causing the inactivation or elimination of other species (disinfecting).

For the purposes of the present invention, the term "disinfecting" relates to reducing the population of any noxious species. (e.g. selective inactivation and/or destruction of disease-causing organisms). The noxious (unwanted) species may be microscopic (e.g. bacteria, viruses, amoebic cysts, protozoan cysts) or macroscopic (e.g. cockroaches, termites, mosquitoes or bats).

For example, it is known that exposure (irradiating) to ultra violet light (at sufficient flux density and appropriate wave length) will kill bacteria and inactivate many organisms or life forms by inactivation or destruction (disinfecting) of essential deoxyribonucleic acid (DNA), and/or ribonucleic acid (RNA) replication sequence/s. Exact details of such groups of noxious species can be easily found in publications released up to date (on the subject of waste water disinfecting) by the Water Environment Federations Research Foundation (WEFRF) and the Environmental Protection Agency (EPA). An example for such microscopic life forms may include spore-forming or non-spore-forming or viruses or bacteriophage or cysts. Some examples are as follows:

Non-spore-forming
*Escherichia coli*
*Enterobacter cloacae*
Direct Total Microbial Count groups
Fecal Coliform group
*Aeromonas hydrophilae/suberia*
*Citrobacter freundii*
*Campylobacter jejuni*
*Thermotolerant coliform* (groups)
Fecal streptococcus group
Heterotrophic (plate Count group)
*Klebisiella pneumoniae*
*Legionella dumofii*
*Legionella pneumophila*
*Mycobacterium avium*
*Staphylococcus aureus*
*Streptococcus faecalis*
*Salmonella typhi*
Fecal streptococci/enterococci
Salmonella spp. group
*Mycobacterium chelonae*
*Mycobacterium fortutuitum*
*Pseudomonas aeruginosa*
*Shigella sonnei*
Total Coliform group
*Yersinia enterocolitica*
Spore-forming
*Bacillus subtilis*
clostridia group
Viruses/bacteriophage
Coxsackievirus B-1 to B-5
Coxsackievirus A-9
Echoviruss 1
Echoviruss 11
H-1 parvoviruss
Hepatitis A virus
Human retrovirus type II
Simian rotavirus
B 40-8 bacteriophage/bacteriodes fragilis
F-specific bacteriophage
Somatic coliphage group
V1 bacteriophage
Polio-1
Polio-2
Polio-3
Reoviruss-1
Reoviruss-3
Cysts
*Cercosporidium parvum* oocysts
*Entamoeba histolytica*
*Acanthamoeba culbertsoni*
*Giardia lamblia*
*Giadia muris*
*Naegleria fowleri*
*Naegleria gruberi*
Macroscopic Species
Cockroaches
Termites
Mosquitoes
Bats Known methods and means for disinfecting liquids or gasses using lamps or laser light sources are limited in their optical distribution efficiency, as well as in their respective design geometry—due to limitations imposed by their respective optical distribution architectures. The known methods and means are not using any optical fibers and crystals, or reflective end—cup interfaces, or semi holographic, partially dielectric rings. Therefore, the known methods are ineffective in delivering simultaneously optical energy to a plurality of points arranged distantly. These limitations impose restriction on the geometry of the known devices so that adequate splitting, distributing, delivery and projection means are not available for these devices. These limitations also prohibit the previous methods from creating, or taking advantage of optical distribution networks for disinfecting liquids or gasses by using at least one central or remote light source. The present invention overcomes these limitations, firstly, by using optical fibers for delivery and distribution and/or diffusing of laser radiation. Furthermore, the present invention delivers optical energy via optical fibers in a primary wavelength for substantial distances before being converted at the end-cup crystal interface. By delivering radiation of the primary wavelength and converting it at the end of the fibers, the present invention provide the following important advantages.

Reducing the damage threshold at the point of entering the fibers by using longer wavelengths e.g. such as a 1064nm wavelength in the IR Spectrum. Such wave lengths are known to be especially suitable for large distance transmission applications in IT and telecommunication optical distribution networks.

Enhancing the delivery capability of optical fibers, eliminating the need to use expensive UV capable fibers such as HGFS (e.g. High Grade Fused Silica) which have only limited UV transmission capabilities.

Making it possible to split the output of a single light source across tens, or hundreds, or thousands of points simultaneously (e.g. in remote locations, or remotely positioned projection, and/or diffusion points) substantially widening design ranges for disinfecting reactors according to the present invention.

The present invention could be used in a wide range of disinfecting application including advanced integrated networks wherein the disinfecting processes occurs at a plurality of points of use, (e.g. such as taps) or at a central reactor (e.g. a conduit or a chamber) of end user points of use. Furthermore, the ability of the method of the present invention to split the laser beam and deliver to a plurality of substantially distanced points, facilitates transmission of wavelengths (e.g. sufficiently short wavelengths) and frequencies of light adequate for production of Ozone (e.g. $O_3$) wherein both designers and end users could benefit from safer geometry with the ability to create a combined multiprocessing network platform for disinfecting liquids and gasses.

Known methods and means for disinfecting liquids or gasses using lasers and lamps will be described in order to emphasize and point out the novelty and inventive progress of the present invention.

References to previous patents, methods and means are included to highlight the inventive steps and evolutionary progress of the present invention.

The present invention is embedded in a novel methodology wherein, unlike previous methods and means, the present invention uses an interactive modular network of optical infrastructure for disinfecting liquids and gasses. Furthermore, the present invention facilitates interconnectivity and interoperability between producers and end users by utilizing the principle of single and/or bi-direction light transmission, harmonic conversion and/or frequency doubling. The ability of the present invention to split and guide light across a local, and/or large area network, is limited only by the efficiencies and/or tolerances such as damage threshold of the materials to be used (e.g. such as coupling and transmission of the laser energy within the damage threshold of the fibers, the crystals, and light sources).

The present invention provides a methodology for delivering light at high intensity across such a disinfecting network, wherein the light is of a particular wavelength (e.g. primary wavelength), and converting (e.g. 2nd, 3rd, 4th, harmonic generation) and/or altering the light at an user end, and/or a point of use into an adequate wavelength thereby maximizing delivery capability of a predetermined dose for effective germicidal effect. The invention utilizes a transfer principle by total internal reflection of optical fibers intermated with crystals for the purpose of carrying light for real time networking between a plurality of domestic, municipal, regional and international environmental protection facilities such as a plurality of disinfection reactors. The facilities comprise water treatment plants, systems positioned, and/or moved across geographically separated locations and/or mobile units positioned on tracks, vehicles, flights, ships, or oceanographic or space stations. The invention allows light which is harmonically delivered, and/or distributed, and/or frequency doubled and or diffused, and or projected via optical fibers to be distributed among a plurality of remote destinations for disinfecting liquids or gasses.

The use of lasers as sources for UV radiation for disinfecting processes is known in the art. For example, the U.S. Pat. Nos. 4,661,264, 4,816,145, 4,265,747 and 5,364,645 disclose disinfecting processes based on irradiation by a UV laser. However, all these patents disclose methods in which the light source itself, i.e., the laser, is attached, or in proximity, or integral to a conduit or chamber wherein the light source is integral to the conduit or chamber, and/or is directly positioned in or against the flow direction. Such devices, according to known methods and means require a complete unit each including a light source, its associated power supply unit, lenses, reflective mirrors or other optical surfaces for laser deflection, making networks of reactors, or remote disinfecting processes economically infeasible (e.g. to disinfect three separated locations in a particular building one must have three light sources etc.).

In contrast, the present invention could be used for a wide range of disinfecting applications in municipal, industrial, domestic, water and air recycling, in industrial cooling towers using liquids or gasses, or at paper, or computer chip manufacturing sites, in medical domains for medical applications requiring selective medical preparations involving liquids or gasses (e.g. blood, plasma, body fluids), in medical or surgical transplants for disinfecting air for hospitals, in air-conditioning systems, in the refrigerator industries, in the food & drink industries, in the semi-conductor, or other precision industries requiring clean rooms to meet predetermined standards, in biotechnology reactors having industrial photosynthesis capabilities, in photosynthesis algae reactors lit, or powered, by solar radiation (sun light which reaches the earth surface after being collimated by the earth atmosphere), in drinking water applications requiring interactive optical fiber and crystal infrastructures or networks for disinfecting a plurality of rooms in a predetermined building. The invention makes it available for the first time a disinfecting optical—network of reactors driven by a single light source (such as a solid state laser), which could be used in agriculture or in drilling wells for water or petroleum, or gas, or combinations thereof, in drilling applications under the surface of the sea bed or in underground wells where there is a need to prevent clogging of filters for liquids or gasses. The invention can also be used in many types of mobile units for intervention task forces operating in disaster areas where damages to infrastructure might have been caused by floods, hurricanes, storms, vulcan activities or earth quakes, or in places where the ground water has been contaminated, or in places where medical aid is not adequate, or available and so the local or regional population must be equipped to deal with the spread of diseases caused by liquids or gasses contaminated by noxious bacteria.

The present invention delivers radiation, using optical fibers and crystal interfaces, liquids or gasses in a plurality of distanced locations from a centrally and/or remotely positioned radiation unit, taking advantage of an interactive optical distribution network for disinfecting the liquids or gasses as well as enabling a widened range of designs for semi-holographic disinfecting reactors (e.g. in or around a predetermined conduits or chambers).

The present invention provides the ability to split the output of a single laser beam (or light source output) into tens, hundreds, or thousands of separated, individually positioned (e.g. fibers distributed within conduits or chambers or around a predetermined space or distance) fibers and/or fiber bundles (terminated with crystals) thereby providing producers and end users in the field with unparalleled flexibility in designing reactors irrespective of the limitations imposed by known methods and means.

The present invention, by utilizing fibers or fiber bundles, is able to provide a plurality of points on a network (locally, or remotely spreading to cover small or large areas) with adequate flux density simultaneously. The invention is therefore geometrically enchanced, more efficient, and/or more economical, thereby requiring less maintenance, and allowing for the transfer and/or performance, and/or delivery of important data acquisition commands across the optical platform in a variety of protocols to and/from a plurality of operating reactors on a predetermined network. More particularly, the invention uses optical fibers for carrying primary and/or secondary disinfecting wavelengths as well as the optical data from sensing peripherals making use of the same fibers and/or bundles to carry the signals back and forth from a remotely positioned control units, in real time. This provides for beneficial advantages in using a single centrally located light source for disinfecting a plurality of different locations simultaneously. The present invention also presents an important level of safety by providing 100% electrical safety given the distance between the light source (centrally, and/or remotely located) and the emitting ends, and/or sides of the fibers, before or after the fibers have been terminated with an appropriate crystal (for performing 2nd, and/or 3rd, and/or 4th harmonics on the primary wavelength originated from the central light source).

The present invention provides a novel methodology for creating an interactive disinfecting network using a single radiation unit to simultaneously deliver light via optical fibers to a plurality of predetermined points (e.g. remotely positioned, and/or separated locations, and/or rooms, and/or channels, and/or taps, and/or a plurality of remotely positioned conduits or chambers).

The ability of the present invention to deliver, through at least one fiber, or fiber bundle (e.g. through a fiber network), a primary wavelength in the IR region and convert the wavelength, at the other end of the fiber by a crystal interface, to a shorter wavelength (e.g. in the UV spectrum) provides for a novel methodology wherein high power could be coupled into the fiber at a long wavelength (such as 1064 nm). Compared to UV wavelengths which are substantially shorter, the long wavelength allows materials which have a lower fiber threshold (e.g. damage thresholds of the fibers) to be used.

Known methods and means using lasers for disinfecting liquids and/or gasses, are limited in their efficiency and ability to provide economically sound, environmentally harmonious, geometrically efficient disinfecting reactors. Known methods and means fail to address the rising needs of today's increasingly stringent standards. Known methods and means using lasers are cumbersome, requiring the laser to emit light in the UV regions of the spectrum. Such lasers are expensive, require introductions of gasses (e.g. in gas lasers, or eximer lasers), often require substantial amounts of periodical maintenance and/or replacements. Known methods and means for using lasers for disinfecting liquids or gasses are geometrically limited, requiring the laser or radiation unit to be positioned in proximity to a conduit or chamber where the liquids or gasses are to be disinfected. Known methods and means require a large number of individual laser (or light source) units for simultaneously disinfecting liquids or gasses in a plurality of remote locations.

Known Ultra Violet disinfecting methods and the means which are used today for disinfecting water (see e.g. Water Environment Research Foundation WERF's "Disinfection Models, Principle Components in UV Disinfecting System Design", 1997) mostly use a large number of individual UV lamps (such as mercury arc lamps) which are arranged into banks of lamps, and inserted into the water. Such methods create cumbersome and often large dimension reactors which requires higher levels of periodical maintenance, and/or a large space for installation. These lamp-based disinfecting reactors have large dimension and weight and are often limited in their mobility, and are not available for large throughput applications as mobile units. These lamps are at present the principle means for generating CW (Continuous Wave) UV energy used for liquid/gas disinfecting. Furthermore, the lamps are polychromatic lamps where up to 85% of the light output is monochromatic at a wave length of about 254 nm which is "considered" to be within the optimum range of about 250 nm to about 280 nm for germicidal effects to take place (e.g. selective inactivation of essential DNA and RNA replication sequences). The known methods and means are expensive requiring a large amount of lamps in a single system. The lamps require periodical cleaning (from colloidal deposits or hard water deposits) using expensive chemicals (e.g. soap or acidic compounds) causing long system down time and high cost maintenance. The lamps which are rigid (inflexible) and immersed in water channels in a large number to form a banks of lamps and are often causing head loss (e.g. places within a conventional UV disinfecting system geometry where water are passing above or below a bank of lamps without being disinfected) and reduction in the efficiency of the known systems, forcing designers to reduce the flow rate through a particular channel and split it over a number of channels. The known methods and means currently used to disinfect water (or air) (e.g. liquids and/or gasses) often require complex and costly mechanical and hydraulic means to lift the lamps in and out of the water, to operate and/or activate brushes on the lamps protecting sleeves (normally made of quartz) periodically, or continuously (for cleaning colloidal deposits and/or hard water deposits), further increasing maintenance cost and energy consumption of the known UV disinfection reactors (systems). Furthermore, systems based on UV lamp technology often require quartz sleeves or other specially formulated transparent protecting tubes or envelopes for protecting the lamps in the water (liquids or gasses). These sleeves often crack from hot spots, generated by the polychromatic characteristic of these lamps (mercury based lamps, usually have sufficient IR radiation in their output to cause heating, which is not uniform due to uneven coverage of colloidal deposits, and or hard water deposits on the surface of the sleeve/s) endangering producers or end users as well as the environment.

It is known that by illuminating a transparent or opaque surface with ultra violet light energy (at the appropriate wave length and sufficient flux density), the UV radiation will penetrate through the surface and according to the nature of that material, the ultra violet light energy would be absorbed into the underlying material. An example of such a process may be: inactivating of DNA and RNA replication sequence/s, by a CW (Continuous Wave) light from a UV microwave excitation lamp, of microorganisms until the flux density of the penetrating light is diminished or absorbed by the microorganisms themselves causing photochemical damages to RNA or DNA within the cells due to the fact that nucleic acids are most important receptive absorbers of light energy. Due to the presence of suspended materials, or organic or non organic surrounding compounds or materials, the level of absorbent energy may be reduced to below the threshold required for effecting disinfection.

The efficiency of devices which disinfect by using ultra violet light is normally restricted by the depth of penetration (UVT or the UV transmission through that material) of the ultra violet light into the material to be disinfected. This factor limits the flow through cross section of the conduit through which the material being disinfected must pass. This factor also prevents ultra violet light from being used to disinfect opaque substances, or limits the capability of distributing UV light to remote locations in industrial or domestic environments over large distances.

The method of the present invention and device according to it eliminate these efficiency limitations. The method of the present invention facilitates the use of a central radiation unit, having a high intensity source of light wherein the light from said radiation unit is distributed, and/or delivered, and/or diffused at points of use (such as end user taps). Unlike the known methods which bring the liquids or gasses to the light (e.g. liquids or gasses are made to pass through the light), the present invention brings the light to the liquids or gasses to be disinfected. Furthermore, the present invention facilitates formation of a novel interactive network of optical fibers and/or crystals for delivering optical energy (of a centrally positioned laser) having a primary wavelength in the NIR, or IR region from about 800 nm to about 2400 nm to remote locations. The primary wavelength is converted using crystals (e.g. such as KTP, or PPKTP types) which generates 2nd, or 3rd, or 4th, harmonics based on the primary wavelength (e.g. 1064 nm).

Therefore, the device of the present invention may be used for disinfecting air, water, (e.g. for drinking, washing, or irrigation applications), drinkable liquids (e.g. juice, milk or vinegar), filterable foods (e.g. baby food, ketchup, or jam), medical preparations, surgical transplants, cosmetics, sewage, waste water, sea water etc.

Furthermore, the device of the present invention is especially adaptable for installation into filtration units such as those which are used for filtering out particulate or suspended materials (suspended solids) from any of the above mentioned substances. This special advantage results from the fact that the device of the present invention distributes the (e.g. ultra violet) light through side emitting optical fibers; wherein the fibers are easily integrated into porous screens or surface disks or membranes or magnetic elements used for filtering.

Another example of lighting disinfection is to illuminate a volume with visible light, in order to disturb the breeding cycle of cockroaches. This type of disinfecting is especially well applicable to sewers, food storage areas, and hollow sections of building members (e.g. in attic spaces, or in conduits for wiring or plumbing).

In principle, each noxious species is disturbed or destroyed by some frequency (at appropriate wave length and flux density) of light.

Thus, since optical fibers (of e.g. end glowing and/or side emitting types) exist for transfer and/or delivery, and/or diffusions of at least one or more wavelengths and frequencies of light from about 180 nm to about 2400 nm, the benefits of disturbing, or destroying, or neutralizing noxious species (in confined and predetermined spaces) may be achieved using the devices according to the present invention. This is an environmental benefit, since all other known methods require introduction of toxic substances such as chlorine or chlorine compounds (e.g. hypochlorous acid or HOCl, hypochlorite ion OCl— or monochloramine, insecticides, pesticides, etc.) which over certain periods of time produce accumulated 1st and 2nd generation compounding volumes which are endangering the man kind and its environment.

SUMMARY OF THE INVENTION

The present invention relates to a method for remote disinfecting liquids and gasses comprising; distributing at least one optical fiber in the region containing the liquids or gasses to be disinfected; aligning at least one radiation unit having a high intensity source of light into the fibers and radiating said liquid or gasses by the optical fiber over a predetermined period of time, wherein the radiation unit is a laser and wherein the primary radiation frequency of the laser is converted to another secondary frequency, before or at the disinfecting site, such that the secondary radiation emitted from the optical fibers has a different frequency from the primary laser frequency. The present invention also relates to a device for disinfecting liquids or gases.

The device of the present invention is comprised of: A device for disinfecting liquids and gasses by the method as defined in claim 1, comprising a conduit or a chamber containing the liquids or gasses to be disinfected, at least one optical fiber distributed within or around or integrated into the walls or the body or the vicinity of the conduit or chamber, and a laser having high intensity source of light aligned into the fibers wherein at least one crystal interface is attached or integrated to at least one optical fiber or bundle of fibers end termination for harmonically converting the wavelength of the incoming primary pulse to a lower wavelength of outgoing pulse.

The device of the present invention is especially useful in filtration units where it can be used as part of a modular (open architecture configuration of parallel or serially interconnecting filters) or as a stand alone module.

DETAILED DESCRIPTION OF THE INVENTION

Figure 1:
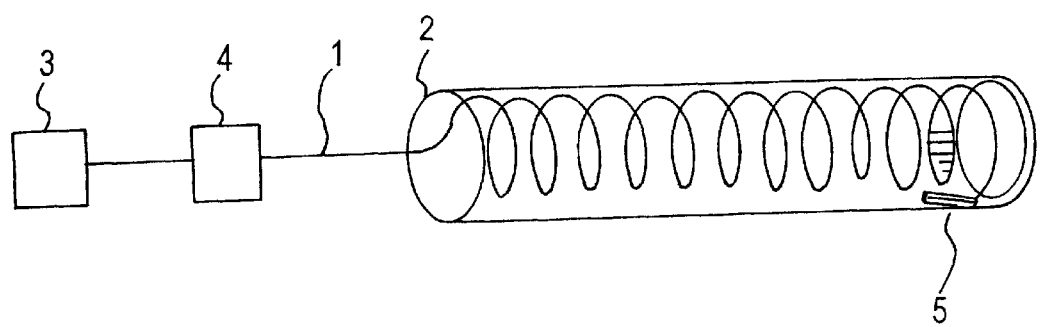
FIG. 1 illustrates a schematic layout of fibers in a conduit.

The present invention also relates to a device for disinfecting liquids or gases, comprising at least one side emitting optical fiber located within a conduit or a chamber, and a radiation unit having a high intensity source of light. The light is lead into the fibers. The fibers are distributed within the conduit or chamber for illuminating a predetermined volume of liquid or gas within the conduit or chamber.

For the purposes of the present invention, a "side emitting optical fiber" is any optical fiber which will transmit light of a desired frequency from one end to the other (using the internal reflection principle), and simultaneously allow some portion of the transmitted light to escape from the fiber during the transmission along the fiber length. Light may escape along the entire length of the fiber, or may be restricted to escape at a plurality of ("exposed") locations along the fiber (examples of such fibers may include high grade fused silica, silica, plastic optical fibers (POFs), polymer matrixes, anaerobic non toxic liquid light guides).

In the context of the present invention "a porous screen" relates to any passive or active element in a filtration system whose function is to prevent particulates of above or below a predetermined size from passing through. Today, filtration screens come in many topological configurations including flat panels, stratified aggregate beds, thin or thick surface disks, perforated cylinders, magnetic elements. A settlement tank, even though it may be used for removal of particulates, is considered a conduit or chamber and not a filtration unit (for the purpose of the present invention). In the context of the present invention, a plurality of end emitting (optical) fibers may be substituted for a side emitting (optical) fiber when the aggregate surface area of the ends of the end emitting fibers is approximately equal to the operational (exposed) surface area of the side emitting fiber; or when the flux density at the appropriate wave length of the delivered light can be otherwise equalized and simultaneously broadly distributed spatially.

In the context of the present invention ultra violet radiation is optical radiation of wavelengths shorter than those for visible radiation, <400 nm (UVA 320 nm–400 nm, UVB 280 nm–320 nm, UVC<280 nm).

In the context of the present invention visible radiation (illumination) is any optical radiation capable of causing a visual sensation directly, 400 nm–>700 nm.

In the context of the present invention uniformity is a measure of how the irradiance varies over a selected or predetermined area (e.g. trance uniform flux density).

In the context of the present invention sun light terrestrial spectra is the spectrum of the solar radiation at the earth's surface, wherein direct solar radiation is the part of extra terrestrial solar radiation which, as a collimated beam/s, reaches the earth's surface after selective attenuation by the atmosphere.

The term "conduit" in the present invention is referring to any space having inlet and outlet openings (e.g. pipes or window frame).

The term "chamber" in the present invention is referring to any space which has one opening (e.g. a container or a storage tank).

In the context of the present invention a "conduit" relates to a predetermined volume such as a chamber which is a closed volume having an opening. A conduit is normally understood as a closed volume having an entrance and an exit, a connector is understood as a closed volume having multiple openings, a closed volume having only microscopic openings or any combination thereof.

In the context of the present invention a plurality of liquid light guides may be substituted for side emitting (optical) fibers when the aggregate surface area of the end of the liquid light guides is approximately equal to the operational (exposed) surface area of the side emitting fiber, or when the flux density at the appropriate wave lengths of the delivered light can be otherwise equalized and simultaneously distributed spatially, or uniformly High grade fused silica and/or liquid light guides having transparent or semi transparent sleeves may be substituted for the side emitting fiber as well.

In the context of the present invention a plurality of side emitting optical fibers may be grouped together in bundles having a common end termination at one end and individual fiber end portions (end terminations) at the other, or they may be looped to have a single common end termination or to form splits (multi-track bundle type having, e.g., single input multiple individual outputs) or formation bundles (distributed within or around or integrated to the walls of a conduit or a chamber having random, rectangular, circular etc. shapes) wherein predetermined species-specific optical dose delivery (flux density required for disinfecting) is maximized for a predetermined radiation unit of a specific spectral distribution.

In the context of the present invention a conduit is any predetermined space with one or more openings for liquids or gases to go into or through or out of the conduit.

In the context of the present invention a chamber is any predetermined space having one opening for liquids or gases to be put—in or out—of or stored or held in (temporarily or permanently) the chamber.

In the context of the present invention peak power is the top most powerful energy generated in a single optical pulse during its duration.

In the context of the present invention pulse duration relates to the overall time span of a single optical pulse (measured by e.g. nano-second often written in short as Ns, pico second written as Ps, fem. seconds written as Fs etc.)

In the context of the present invention pulse repetition rate relates to the number of pulses generated over a predetermined time (measured by e.g. pulses per second, normally measured in Hz, for example from about 10 Hz to about 18,000 Hz). Furthermore, in the context of the present invention said pulses are launched into optical fibers each having at least one crystal and/or lens at its end termination interface.

In the context of the present invention pulse wavelength relates to the specific wavelength in which a predetermined pulse is being generated, or projected, wherein pulses so generated within the laser could have different wavelength when exiting or projecting from the fiber (or bundle of fibers) end termination/s, through the crystal interface (e.g. a holographic element).

In the context of the present invention wave length range relates to the range of wave lengths generated by a predetermined monochromatic or polychromatic light source or any combination thereof. Furthermore, the resulting range of wave lengths transmitted or dispersed or emitted or irradiated or illuminated or refracted or reflected, or any combination thereof, through (at least one) predetermined optical fiber or bundle/s.

Utilitarian utilization of a predetermined wave length, or beneficial spectrum-specific context or range or band or plurality of wave lengths or associated cut-off frequencies from groups of predetermined transmitting materials, or substances-associated cut off frequencies of light, relates to at least one CW or PW e.g. Continued Wave or Pulsed Wave light energy source outputs or inputs which are or exited or lased or harmonically generated by at least one crystal or filtered, or any combination thereof, and lead into a predetermined volume of liquids or gasses within a conduit or chamber.

In the context of the present invention pulse modulation relates to the amount or type or timing or combinations of predetermined modulation modes (e.g. control changes or timing changes or frequency changes or level changes or any combination thereof) applied to a specific pulse or sequence of pulses before or during or after or in accordance with a process or plurality of pulse generation processes used in a specific light source or sources or their associated control electronics and integral or non-integral power sources.

In the context of the present invention down conversion relates to any optical process or plurality of processes in which a primary higher wave length pulse is converted (e.g. down converted to its harmonics) to a lower wave length or harmonics by the use of a predetermined crystal or any predetermined optical element (e.g. this process often called harmonic generation for example a 2nd harmonic on a 1064 nm [IR] pulse will be 532 nm [Vis] etc.

In the context of the present invention 2nd, or 3rd, or 4th harmonic generation also relates to inter-cavity harmonic generation processes which occur within a predetermined laser cavity by at least one integrated, or externally attached, or supported crystal, or a plurality of aligned, or coupled sequentially interconnected crystals (e.g. when the light source is a laser).

In the context of the present invention triggering means activating or deactivating or controlling or any combination thereof of a parameter or plurality of parameters related to creation and generation of a specific predetermined pulse transmitted in real time through at least one optical fiber (or any predetermined sequence or plurality of sequences of a predetermined number of pulses) over a predetermined time (through the fibers).

In the context of the present invention up conversion relates to any optical process or plurality of processes in which a primary lower wave length pulse is converted (e.g. up converted to its harmonics through excitation and use of crystals) to a higher wave length or harmonics by using a predetermined crystal or any predetermined additional optical element or material in a given state (e.g. liquid, solid, gas) which are inherently excitable. This process often called harmonic generation and is performed with the aid of predetermined crystals or additional optical elements, e.g. SHG, THG, FHG, etc.

In the context of the present invention a crystal end-cup is any crystal attached to or integrated with, or integral, or supported by, or positioned in proximity to the end termination of a fiber for efficient 2nd, and/or 3rd, and/or 4th harmonic generation therefrom (e.g. for illumination or irradiation of a predetermined volume of liquids or gasses in the conduit or chamber).

According to a preferred embodiment of the device of the present invention, the device includes a conduit or chamber where the fibers are distributed and/or includes means for supporting or maintaining the distribution of the fibers within the conduit or chamber.

According to one especially useful embodiment of the device of the present invention, the light is primarily ultraviolet, for disinfection (selective inactivation or destroying) of bacteria or other microorganism life forms.

Light from the radiation unit is lead to the optic fiber by optically aligning a beam of light from the radiation unit into an end termination (end portion) of the fiber, or by integrating the radiation unit into the fiber, or by optically aligning beams of light from the radiation unit into (through) a side of the fiber.

According to a preferred embodiment of the device of the present invention, the conduit or chamber is a filtration unit having at least one porous screen or (element) surface disk for removal of particulate material. Furthermore, the optical fibers may be integrated into or onto at least one of the screens or surface disks (e.g. filter elements).

There may be environments which cause deterioration to the surface of the optic fibers. This deterioration may be caused by physical contact (such as high velocity impact of particles and the fiber's surface) or by chemical reactivity between the fiber's surface and liquids (or gases) in the conduit or chamber.

In such cases it is advised to isolate the fibers from their operating environment by using a transparent or opaque sleeve. Thus, one embodiment of the device of the present invention has a separate transparent or opaque sleeve enclosing the optic fibers, while in another equally useful embodiment the sleeve enclosing the optical fibers is integrally formed.

According to another useful embodiment of the device of the present invention, the light is primarily visible, especially for disturbing the breading cycle of cockroaches.

The selection of light source (for production of visible light and/or ultra violet light and/or light of other wave lengths and frequencies) depends on the target species and to their wave length and frequency specific light sensitivity. For example, according to a novel embodiment of the device of the present invention the conduit or chamber of the device (or the conduit or chamber where the fibers of the device are distributed) is a sewer pipe, a section of a sewer pipe, or a network of sewer pipes.

According to this embodiment, bacteria and/or cockroaches and or other noxious species may be eliminated from (disinfected e.g. selectively inactivated or destroyed) the sewage prior to (or during or after) standard treatment and/or discharge.

This treatment of the sewage while still in the sewer pipe network is especially useful for improving public health (a) in large urban areas where many regions of the sewage collection network are distant from their eventual treatment plants, (b) in regions where the eventual sewage discharge is through a cesspools (distributed local ground seepage networks) and where simultaneously the ground water level is high, and (c) in urban areas where the human population does not have proper access to modem medical care (and is thus subject to epidemic noxious infestations), (d) intervention task forces to disaster areas and regions which may experience floods, typhoons, hurricanes or earth quakes and are therefore in need of urgent disinfecting of liquids or gases due to collapsed or damage to existing infrastructure (e.g. water pipes and treatment plants, important air passages), (e) sea water filtration systems, (f) pre/post filtration for sterilization (g) pre/post disinfecting of industrial water recycling.

Another useful embodiment of the device of the present invention relates to the conduit or chamber (where the fibers are distributed) as a closed space. For example, when the closed space (conduit or chamber where the fibers are distributed and /or are supported) is (a) the aeration volumes of loosely packed soil, (b) a cabinet, (c) a closet, (d) the space below a raised floor, (e) the space above a drop ceiling, (f) the space in a hollow wall, (g) an attic, (h) a crawl space, (i) the space between stored articles, (j) the space between infrastructure support connections (e.g. underground, electric or telephone cables), (k) a water carrying pipe or module, (l) a shoe (when not being worn), the space in a brush head for cleaning conduits or chambers, (m) a window frame to the open air, (n) a tunnel, (o) oxygenation and water treatment ponds, (p) the head of a tooth brush, (q) a vacuum cleaner attachment.

Many of the embodiments of the device of the present invention are functionally more efficient when they have a computer controlling the output of the radiation unit. The computer may effect this control by regulating the electric current powering the radiation source (for certain type of light sources), by regulating the alignment of light from the radiation unit with the side emitting optical fibers, or by regulating the reflective feed back of the terminal end cap at the far end of the side emitting optical fibers.

According to a preferred embodiment of the device of the present invention, the radiation unit is a laser. According to a further refinement of the preferred embodiment of the present invention, the optical fiber's path in a predetermined space of the conduit is arranged to form at least one region of constructive interference in the conduit where liquids or gases are present (and this result is most conveniently accomplished when the radiation unit is a laser).

This constructive interference is easier to accomplish in a controlled geometry when the fiber's path (according to the present invention) is of a spiral (or zig-zag) arrangement for forming a plane, a cone, a cylinder, or a smooth surface.

Another compatible method wherein the constructive interference is accomplished is to arrange the path of the fiber with the fiber bent back along its own path to form at least one section of parallel fiber path.

A further compatible method for use of the device of the present invention wherein the constructive interference is accomplished is to arrange a reflective member parallel to at least one section of the fiber in the conduit or chamber.

According to a preferred embodiment of the device of the present invention, this reflective member is integral to the at least one fiber.

According to another useful embodiment of the device of the present invention, the end of the optical fiber or fibers in the conduit or chamber are arranged to form at least one region of constructive interference in the conduit or chamber (when the radiation unit is a laser). A preferred method for accomplishing this effect according to this embodiment is to arrange the end of at least one of the optical fibers opposite a reflective member.

According to another embodiment of the device of the present invention, a holographic optical element (e.g. a computer generated film, digitally encoded memory chips or disks) is incorporated into the means for aligning the sheath of the fiber (in the conduit, a chamber) to form at least one region of constructive interference in the conduit or chamber (when the radiation unit is a laser).

For example, according to one method of using the device of the present invention the holographic element is aligned between the radiation source and the end of the optical fiber, or according to another method of using the device of the present invention, the holographic element is located in the conduit or chamber at the terminating end of the optic fiber. The use of holographic elements especially outside of the visible spectrum (such as in many applications of the device of the present invention) allows an invisible hologram (e.g. uv hologram within the conduit or chamber) to be formed.

According to another interesting embodiment of the device of the present invention, a reflective end cap is affixed on the terminal end of the optical fiber to form at least one region of constructive interference in the conduit or chamber (when the radiation unit is a laser) to be formed.

According to another embodiment of the device of the present invention, a disinfecting holographic element is formed within a conduit or a chamber using at least one (side emitting) optical fiber wherein the holographic formation is brought by at least one single wave length coherent light beam at about 187 nm to about 320 nm wherein focusing optics are used for conditioning the light beams (from the radiation unit) on entrance or exit to/from the fiber.

According to an environment friendly embodiment of the device of the present invention, a plurality of fibers are aligned to at least one radiation unit having a high intensity light source. The fibers are distributed within a conduit or a chamber wherein the fibers are grouped by a common end termination at one end, and their other end portions are grouped together to form a brush. Light from the light source is illuminating outwardly from the fibers sides and end portions for illuminating a predetermined volume of liquids or gases internally, i.e. within the brush head or externally, i.e. within an external conduit or chamber.

According to an embodiment of the device of the present invention, end portions of a plurality of (side emitting) optical fibers are grouped and harnessed to a common end termination within a modular attachment of a vacuum cleaner wherein other ends of the fibers are grouped together in the shape of a (fiber) brush. A radiation unit having a high intensity source of light is aligned with the fibers, wherein the fibers are distributed within the conduit or chamber for illuminating a predetermined volume of liquid or gas therein.

According to an embodiment of the device of the present invention, at least one high power ultra violet laser is used in at least one of pulsed mode and continuing mode (pw, cw) and combination thereof, and the ultraviolet pulses and continuous waves are referenced, controlled and triggered by an accurate clock for illuminating a predetermined volume of liquid or gas within a conduit or chamber.

According to an embodiment of the device of the present invention, light from at least one light source is aligned to at least one multiplexed, multi-dimensional distributed layer of a side emitting optical fiber for the purpose of removing or self cleaning (by photons optical impact) colloidal deposits and/or hard water deposits from immersed fiber/s sleeves, optical outputs, reflectance members, conditioning optics, light guides, or a combination thereof, by providing an enhanced ultra violet transmission from about 180 nm to about 280 nm within the conduit or chamber thereby ensuring that the UV dose delivery is calibrated in accordance with species-specific calibration standards for adequately illuminating or irradiating or disinfecting a predetermined volume of liquid or gas within the conduit or chamber.

According to an embodiment of the device of the present invention, at least one region of constructive interference (holographic) at a preferred wavelength in the range from about 180 nm to 270 nm and the flux density are calibrated in accordance with the species-specific calibration standards wherein DNA or RNA replicating sequences of at least one micro-organism or at least one macro organism or a combination thereof is selectively inactivated.

According to an embodiment of the device of the present invention, at least one high intensity light source is positioned at a predetermined distance from the conduit or chamber wherein the light is guided or launched or projected or trajected or transferred or diffused or any combination thereof by at least one side emitting optical fiber for the production of at least one region of constructive interference within the conduit or chamber. The device of the invention should not physically restrict water or gas movement or flow in, out of or through the conduit or chambers.

According to an embodiment of the device of the present invention, the fibers are distributed within and around a plurality of optically transparent (water) filtering disks, screens for simultaneously filtering suspended solids in a pre determined volume of liquid or gas continued in a conduit or chamber while illuminating or irradiating the liquid/gas.

According to an embodiment of the device of the present invention, at least one radiation unit has a high intensity source of light, and the light, pulsed or continuous or a combination thereof (at about 180 nm to about 400 nm) is aligned to a plurality of side emitting optical fibers and the fibers are distributed within a conduit or a chamber for illuminating a predetermined volume of liquid or gas therein. An adequate level of particle size distribution (PSD) is reached (by pre filtering or recycling of the liquids or gases) to ensure continuous (adequate) transmission of optical radiation of a specific spectral distribution over a predetermined period of exposure time (e.g. disinfecting dose).

According to an embodiment of the device of the present invention, the radiation unit having a high intensity source of light is a fiber laser wherein the fiber laser could be ergonomically integrated into a tight space inside or outside of a conduit or a chamber.

According to an embodiment of the device of the present invention, the conduit or chamber is a filtering unit having at least one magnetic element or field for filtering out metallic substances or compounds (in the liquids or gases to be disinfected).

According to an embodiment of the device of the present invention, conditioning optics (e.g. a lens, a beam spliter, an acousto-optical shutter, a shutter, a focusing lens, a beam expander, a beam expander telescope) are used to condition beams of light (from the radiation unit) exiting from the fiber.

According to an embodiment of the device of the present invention, an off axis beam or reference beam is projected from end portion/s of at least one side emitting optical fiber wherein the fiber end portions are distributed within a conduit or a chamber for production of at least one region of constructive interference (within the conduit or chamber).

According to an embodiment of the device of the present invention, an ultra violet (invisible) hologram is formed within a conduit or a chamber from at least one region of constructive interference for facilitating elimination of head loss due to the conduit or chamber geometry (without distracting the liquids or gasses flowing therethrough).

According to an embodiment of the device of the present invention, the level or flow rate of liquids and gases within a conduit or a chamber is calibrated to a radiation unit for saving on energy consumption or maximizing the efficiency of illumination or irradiation of a predetermined volume of the liquids or gasses within the conduit or chamber.

According to an embodiment of the device of the present invention, the conduit or chamber where the fibers are distributed is water or air systems in a car (e.g. air conditioning, radiator, wind shield washing system).

According to an embodiment of the device of the present invention, the conduit or chamber where the fibers are distributed is water or air (liquid or gas) systems in a public transport train or bus.

According to an embodiment of the device of the present invention, a high intensity IR pulsed light source launches pulses at a repetition rate from about 10 Hz to about 1 Ghz, a pulse width of from about 118 Ps to about 100 ns and a wavelength of from about 850 nm to about 2400 nm. The pulses are launched into single mode fibers. A connected or integrated crystal is aligned at the end point of the single mode fibers (the end termination entering into the reactor active cross sections) for creating 4th, or 3rd, or 2nd harmonics or any combination thereof, thereby for illuminating or irradiating a predetermined volume of liquids or gasses within the conduit or chamber with a wide range of spectral signatures.

According to a preferred embodiment of the present invention, at least one fiber is a PM (Polarization Maintaining optical fiber) type fiber having its polarity calibrated against the polarity of the crystal or a plurality of crystal interfaces for maximizing the conversion efficiency along a predetermined optical axis, or in the direction of the optical path or in accordance with a predetermined conduit or chamber geometry predetermined optical fibers, crystals and laser disinfecting reactors.

According to a medical application of the present invention, a predetermined conduit is used for external dialysis processes wherein fibers are distributed around and/or supported on the conduit for illuminating or irradiating a predetermined volume of liquids or gasses therein. Furthermore, the liquids or gasses could be illuminated or irradiated in a wide range of medical treatments including: 1) Preparation of pharmaceutical substances or medicines, 2) Medical discharges e.g. during operations or other procedures, 3) Invasive medical procedures using laser operation, 4) Birth procedures for general hygiene, 5) Dentistry or orthodontist procedures and treatments, 6) Darmatological treatments 7) For disinfecting the air or water supply to and from numerous hospital patients, 8) Infusion of liquids or gasses, 9) Transplant operations, 10) Medical transplants 11) Incubators for young or prematurely born babies, 12) For disinfecting clinic or laboratory liquid or gas main supplies, 13) In aquariums or other life preserving conduits or chambers, 14) In emergency equipment for resuscitation, 15) In a rural or urban main supply of liquids or gasses to hospitals or domestic or industrial end users, 16) In clean rooms or environments used for diagnostics or medical treatments against noxious species.

According to a medical application of the present invention, small or large medical instrumentation can be disinfected efficiently. More specifically fiber crystal end terminations are distributed in or supported by or integrated into or placed in a proximity of or connected to a conduit or chamber. Predetermined pulse peak powers or pulse frequencies are utilized for specific equalization or inactivation of noxious species in: a) disinfecting tank or area or chamber, b) a working area where liquids or gasses are presented, c) a stove or table surface, d) a window frame or air passage, e) air-conditioning systems or air pumps, f) laundry areas and storage containers, g) semi-conductor manufacturing sites or rooms, h) laundress, i) food storage tanks or containers or rooms, j) drinks and beverages manufacturing conduits or chambers, k) conduits or chambers for dissemination of sea water, l) biologically controlled environments such as laboratories and their associated storage conduits or chambers in biotechnology industries, m) conduits or chambers used for the dairy industry and related food produce industries, n) Hygiene or educational predetermined areas or surfaces wherein contamination of bacteria may occur in conduits or chambers or in confined predetermined containers storage areas, o) in conduits or chambers for preparation of baby foods or drinks, p) in medical emergencies when it is needed to immediate disinfect of a predetermined conduit or chamber or surface used in a specific medical operation or procedure, q) in beds or mattresses wherein a predetermined conduit or chamber is to be used for transferring or distributing or disinfecting liquids or gasses contained therein, r) in "at source" liquids or gasses at points of origination, s) in paper factories, t) in swimming-pools, w) in industrial recycling of liquids or gasses, x) in air treatment plants, y) in critical air passages, z) at the end user point of use of drinking water, z/a) at the end user point of use of air or other relevant unharmful gasses during medical treatments and procedures.

According to an embodiment of the present invention, a high intensity pulsed light source is down or up converted e.g. by $2^{nd}$, or $3^{rd}$, or $4^{th}$ harmonic generation and/or excitation, and/or pumping architectures or any combination thereof at one end of the fiber and harmonically processed, or converted, or excited, or any combination thereof at the other end of the fiber for illuminating (in 400 nm to 700 nm visible spectrum) or irradiating (in 850 nm to 2400 nm and 200 nm to 400 nm spectrums) a predetermined volume of liquids or gases within the conduit or chamber (e.g. within active reactor geometry, or holographic type ring, or slits, or bar, or any combination or arrangement thereof).

According to an embodiment of the device of the present invention, the high intensity light source is a pulse laser which is used to provide primary pulses in the infra red (IR) portion of the spectrum. The pulses are launched or distributed or transmitted through single mode fibers, or multi-mode fibers, or gradient index fibers, or light conducting layers, or any combination thereof to be converted or harmonized to produce UV (A, B, C) or visible light or IR for illuminating or irradiating a predetermined volume of liquids or gasses in the conduit or chamber.

According to an embodiment of devices according to the present invention, light from a pulsed laser (e.g. high intensity, high energy, high peak power pulsed laser light) is converted into 2nd harmonic, or 3rd harmonic, or 4th harmonic (e.g. SHG, THG, FHG, etc.) using a predetermined primary wavelength according to predetermined lazing materials, or mirrors, or prisms, or lenses or any combination thereof (e.g. by a crystal positioned at a predetermined angle). Furthermore, in an especially beneficial embodiment of the device of the present invention the harmonic generation processes are performed within a predetermined area of the cavity (or cavities) in a predetermined laser light source geometry, prior to delivery of the high intensity or high peak power laser pulses at least one optical fiber or bundle of fibers (e.g. using inter-cavity SHG, THG, FHG), for efficiently illuminating or irradiating a predetermined volume of liquids or gasses within the conduit or chamber.

An embodiment of the device according to the present invention has at least one flash lamp as the primary pumping (e.g. optical pumping) of the laser (e.g. lazing rod). A further beneficial embodiment of the present invention has at least one diode as the pumping (e.g. optical pumping) of the high peak power light source.

In an embodiment of the device of the present invention, the primary (e.g. pumping) wave length is selected from about 1064 nm for Nd:yag/1064 nm or GaAs/810–905 nm or any combination thereof for efficiently illuminating or irradiating using a crystal interface to generate 2nd or 3rd or 4th harmonics whereby a predetermined volume of liquids or gasses in the chamber is adequately disinfected using short pulses having high peak powers in contradiction to CW average power which is generated by UV lamps which are currently the principle means of generating UV energy for disinfecting.

In a preferred embodiment of the device of the present invention, the pumping wave length is selected from a predetermined electromagnetic spectrum wherein each laser according to the lasing material corresponds to appropriate crystals for generating 2nd or 3rd or 4th harmonics or any combination thereof. The pick power of the primary or harmonic pulses provides for efficient illumination (in a visible spectrum 400 nm to 700 nm) or irradiation (in spectrums of 220 nm to 400 nm for UV radiation or 700 nm to 2400 nm for IR radiation) of a predetermined volume of liquids or gasses by providing an adequate dose of pulses peak powers to efficiently inactivate DNA and RNA replication sequences.

In an embodiment of the device of the present invention, the conduit or chamber inner surface is grooved, or bent, or deposited or extruded or injected or glued or inserted or extended or pulled by a variety of fashions, or coated spirally or deposited in layers, to extend inwardly in a predetermined patterns for the purpose of guiding hydraulically or pneumatically a predetermined volume of liquids or gasses therethrough. More specifically, the extensions can take the shape of (A) a spiral extending to cover at least one portion of the predetermined inner space along the length of the conduit or chamber for slowing or speeding the movement of the liquids or gasses therethrough or (B) a grid uniformly ditributed in the conduit. The liquids or gasses are permanently or temporarily standing or stored in, or in transition in and throughout the conduit or chamber, or any combination thereof. The fibers or wave guides are distributed for effective illumination or irradiation of the liquids or gasses over a predetermined time.

A preferred embodiment of the present invention is especially useful where the conduit or chamber is integral parts of a vehicle. Furthermore, the engine or power source of the vehicle could function or be diverted for operating the pulse or continuous laser source or pump or water or air flow or any combination thereof. Furthermore, the engine could operate in a single platform in which the flow rate or velocity or pressure or quality of the liquids or gasses will control the pulse width or pulse duration or pulse peak power, or pulse wave length or pulse repetition rates or any combination thereof of the laser.

A further useful embodiment of the device according to the present invention is to have a vehicle equipped with a high intensity pulse laser light source connected to the batteries or engine of the vehicle for illuminating or irradiating a predetermined volume of liquids or gasses in the integrated conduits or chamber.

In a preferred embodiment of the present invention, laser pulse repetition rate (1) or pulse duration (2) or pulse peak-power (3) or pulse-wavelength (4) or pulse width (5) or any combination thereof are synchronized or locked or referenced or timed or triggered or controlled or modulated by (when connected to a computer) software or hardware or any combination thereof.

Furthermore, water flow (6) or air flow (7) rates or any hydraulical or pneumatical aspects or parameters relating to the flow of liquids or gasses in the conduit or chamber or any combination thereof are linked to refer (8), or activate (9), or control (10), or modulate (11) a predetermined variety of control parameters from the active light source power unit (12), or its associated control electronics (13) for generating high peak power pulses (e.g. harmonic generation by attached or integrated crystals into the fiber end termination) or for production of timing variation (14) or sequences of variations (15) in laser pulse duration (16), or width (17), or repetition rates (18), or peak power (19), or pulse wave length (20), or angle (21), or any combination thereof when the attached or integrated crystal (22) is positioned inside a ring (23) or rod (24) or pipe (25) or network of infrastructure supports (26) or flat or curled or twisted or pressed surfaces or any combination thereof. Furthermore, in an especially beneficial embodiment of the present invention, a plurality of parameters are software controlled such as TSS (26a) (Total Suspended Solids) levels or Turbidity levels, (26b) PSD or Particle Size Distribution levels, liquid or gas flow rates (27) or any combination thereof. The parameters are detected (28) in real time and/or synchronized (28a), to ensure continuous (29)(adequate) transmission of optical radiation (30) of a specific spectral distribution (31) over a predetermined exposure time (32) e.g. disinfecting dose using the peak powers (33) of the pulses or sequences (34) of pulses.

In an especially beneficial embodiment of the device of the present invention, a plurality of predetermined (variables) parameters or aspects or levels or time positioning of any combination thereof relating to the laser pulse generation device (e.g. high intensity pulse laser light source) are interacting in real time for the purpose of illuminating or irradiating a predetermined volume of liquids or gasses over a predetermined time in the conduit or chamber. Furthermore, the device of the present invention utilizes a high intensity pulse laser source having associated hardware or software architecture linked or synchronized to hydraulic or pneumatic aspects or parameters associated with the flow rate of the liquids or gasses or related to the predetermined types of the liquids or gasses being disinfected or any combination thereof.

In an embodiment of the device according to the present invention, at least one conversion process, or plurality of processes, is taking place within the laser head itself in order to maximize transmission, or minimize fiber damage thresholds or tolerances, or any combination thereof. Furthermore, in an especially useful embodiment of the present invention a 2nd, (or 3rd, or 4th,) harmonic generation device is placed in the vicinity of the laser enclosure (or head) wherein the laser in its entirety is irradiating or illuminating into (coupled) at least one optical fiber at a wavelength of from about 218 nm to about 1064 nm and the wavelength is converted at the other end of the fiber into an adequate wavelength or frequency of light, using at least one crystal or a plurality of crystals, for irradiating or illuminating a predetermined volume of liquids or gasses in the conduit or chamber with the light.

In an embodiment of the present invention, the laser pumping architecture is a) a flush lamp, b) a diode pumping architecture, or any combination thereof. Furthermore, in an embodiment of the present invention, at least one high intensity pulsed laser source of light (A1) is aligned to a predetermined fibers matrix thread (B1) or multi track bundle of fibers (C1) or rectangular bundle of fibers (D1) or single mode arrangement of fibers (E1) or multi mode common end termination holding a predetermined number of single strand fibers (F1) or group or mixed groups of fibers (G1) or predetermined dimensionally positioned polarization maintaining arrangement of fibers (H1) or graded index collection of fibers (I1) or multiple gradient index fibers held together (J1) or any combination thereof (K1). The fibers are aligned with the output of the high intensity, high peak power pulse laser light source for receiving pules (L1) or sequences of pulses (M1) each having high peak powers. The variables or parameters relating to the different relationships between the flow rate of predetermined liquids or gasses (N1) through a predetermined conduit or chamber (O1) geometry or cross section or length or dimension over a predetermined time (P1) are associated with aspects of light (Q1) i.e. associated pulsed or continuous (e.g. PW, CW) modes (R1), velocities, or energies, or timings or any combination thereof.

Furthermore, in an embodiment of the present invention, the fiber end terminations are distributed and/or supported with crystal interfaces or end cup inputs/outputs which transmit light but isolate, protect and block the passage of liquids or gasses from within or throughout the conduit or chamber from reaching out through the optical fiber input/output interfaces or gaps therebetween or any combination thereof (e.g. crystal interfaces, end cups, lens, beam expanders, mirrors, elastic siloxan based lens which are straight, bent, twisted or any combination thereof). The supports including a) a ring, b) a rod, c) a straight section of metal, or d) plastic or e) polymeric compounds or f) rubber silicon or g) flat diluted rubber silicon, h) conduit or chamber, i) single or double or triple or any combination there of opaque or reflective walls or enclosure of a disinfecting reactor (e.g. a conduit or a chamber). Furthermore, the support for the optical fiber integrated j) crystal end terminations could be positioned in a predetermined parallel k) or sequential l) output path corresponding to the geometrical shape or the specific dimensions of the predetermined conduit or chamber types, the direction m) or flow velocity n) of the liquids or gasses in the conduit or chamber. This embodiment comprises a variety of supports and guiding elements including o) hydraulic spiral inner extension or steering having predetermined shapes or grooves, pneumatical steering wings or shaped extensions p) for conducting and circulating the liquids or gasses across the cross-section of the conduit or chamber for increasing their respective predetermined exposure time (e.g. slowing down flow rate by conducting the liquids or gasses around (by increasing friction or resistance equilibrium), q) a pipe or network of pipes, r) a grid, s) a network of grids, t) a conduit or chamber, w) a pond or tank x) a mobile vehicle for intervention task forces specialized for disaster suffering areas caused by floods, earth quakes, vulcan activities y) a conduit or chamber for medical preparations, and/or transplants, z) medical dialysis of blood and air or other related, and/or relevant liquids or gasses.

In an embodiment of the device of the present invention, the same single mode fiber or fiber bundle used to distribute high intensity pulsed energy (prior to performing $2^{nd}$, $3^{rd}$, $4^{th}$ harmonic generation) is simultaneously used to carry sensored data or spectroscopic data acquisition or other relevant data or machine control protocols or any combination thereof, for monitoring of illumination or irradiation or for transferring measurements of a predetermined level of suspended solids or biological compounds or non-biological compounds or turbidity or transparency or any combination thereof in a volume of liquids or gasses inside the conduit or chamber.

In an embodiment of the present invention, liquids or gasses are illuminated or irradiated or transferred simultaneously within the same reactor geometry.

In an embodiment of the present invention, the crystals are attached or interfaced to the end termination of the fiber or fiber bundle the predetermined bundle of fibers is coated for appropriately providing sufficient electrical conductivity to change the magnetic charge of the surface of the crystal for the purpose of creating repulsion from the illuminating or irradiating (e.g. pulsed or continuous modes PW, CW) or slowing or preventing the attachment or any combination thereof of colloidal deposits originating from or carried by hard water or air or other liquids or gasses within the conduit or chamber.

In an embodiment of the device of the present invention, at least one short laser pulse having a high peak power from a high intensity source of light is more efficient, over the same period of time for the purpose of providing an adequate disinfecting dose against noxious micro organism, than an average power of a CW/UV lamp of the same rated power output. Furthermore, in an embodiment of the device of the present invention, inactivation of DNA or RNA replication sequences are inferred with as a result of illumination of the short pulses having high peak powers in the visible spectrum or the UV (A, B, C) spectrum or the IR spectrum or any combination thereof.

In a preferred embodiment of the device of the present invention, at least one laser pulse has a short duration of time from about 1 arc/sec to about 1 second and the laser pulses has a high peak power of from about 118 mJ to about 3.18 J. The pulses are radiated into a conduit or chamber through optical fibers wherein the short laser pulses having high energy are directly projected or targeted or reflected or transmitted or any combination thereof to ensure continuous (adequate) transmission of optical radiation of a specific spectral distribution over a predetermined exposure time (e.g. pulse disinfecting dose or PDD). Alternatively, the pulses are distributed throughout the entire length of the fiber for illuminating and/or irradiating a predetermined volume of liquids and/or gasses within the conduit or chamber. The ability to manipulate and deliver light from the light source to a predetermined location within a predetermined reactor (e.g. a conduit or chamber), and to split, and/or transmit, and/or diffuse, and/or deliver, and/or project and/or harmonically generate predetermined wavelengths of light or any combination thereof from a single light source, surpasses previous methods of delivering an adequate disinfecting dose without fibers. Furthermore, previous methods of laser delivery have not satisfied producers and/or end users with sufficient efficiencies of optical distribution and have not entered the market due to above mentioned limitations due to reactor design constrains. Furthermore, the present invention gains many advantages by being capable of splitting the light from a single light source over hundreds and/or thousands of individual optical fibers, facilitating accurate delivery of optical energy to any location within a reactor (e.g. a conduit or chamber) geometry, leaving the lamps or lasers out of the reactor vicinity, allowing creation of important networks of optical fibers for carrying, delivering and distributing high intensity optical energy to points of use, and/or end users from a central or remotely positioned light source. The present invention facilitates an advantageous, novel, and utilitarian beneficial system geometry, and/or architectures wherein instead of current technologies for disinfecting bacteria which brings the water to the light; the present invention delivers the light to any predetermined locations through/via optical fibers. The light will be converted into an adequate wavelength and/or frequency range, or down converted, and/or harmonically generated for efficiently illuminating and/or irradiating a predetermined volume of liquids or gasses in the conduit or chamber provided with the fibers.

In a preferred embodiment of the device of the present invention, in order to disinfect a predetermined volume of liquids or gasses (within the conduit or chamber), the fibers are distributed around or supported by, or attached to, or connected to, or embedded in, or glued to, or sucked in the conduit or chamber, by a reversed pressure, or a flow pressure, or a pressure relating to the depth of the liquids (e.g. water),or gasses (e.g. such as air), or solids (e.g. such as soil), or rocky layers e.g. often found in oil fields or petroleum wells or drilling sites.

In a preferred embodiment of the present invention, the conduit or chamber is the filtration unit in wells for filtering suspended solids in petroleum, and/or water drillings sites on the ground and in the sea where conventional existing technologies fail to provide appropriate economically realistic solution to noxious bacteria responsible for clogging water filter grids, or matrixes, or conduits or chambers, or water cooling filter elements for drilling heads in a predetermined drilling site. The present invention is not so limited and could also be used in a wide variety of drilling applications where high repetition rate, high peak power pulses (a1) could be launched (b1) hundreds of meters under the sea (c1) or deep in the ground (d1) via or through an optical fiber (e1), or a bundle of fibers (f1). At the target destination light is passing through an end cup or a crystal interface for harmonic generation therby delivering a predetermined wavelength of light into a conduit or chamber (e.g. the water filter for cooling the drill heads, deep under the sea bed or ground) for illuminating or irradiating a predetermined volume of liquids or gasses therein (with the light).

In a preferred embodiment according to the method of the present invention, any combination of liquids or gasses enclosed inside a natural conduit or chamber (e.g. inside earth layers or rocky layers) can be disinfected. A drilling site could be under water (1), in the open sea (2), in wells for fresh water (3), or petroleum wells in variety of topographic or geophysical locations (4). Furthermore, a wide variety of geometry could be beneficially used therby increasing efficiency of the drilling sites by providing efficient means for disinfecting bacteria or noxious microorganism which clogs important existing filtration paths and means (5).

In an embodiment of the device according to the present invention, a remote high intensity, high pulse peak power laser light source (6) is coupled (7) to a predetermined arrangement of a single mode fiber (8), or a plurality of fibers bundled (9) in a predetermined shape (9a) or packing friction (10) or any combination thereof (10a). The predetermined fiber types are chosen to carry adequate intensity of pulsed energy (10b) for irradiating or illuminating a predetermined volume (10c) of liquids or gasses in the conduit or chamber.

In a preferred embodiment, a group of devices according to the present invention, is especially beneficial in drilling sites for underground survey for predetermined petroleum liquid types (12) or fresh water (13), or liquids (14), or gasses (15), or any combination thereof (16) (in such drilling sites at least one type of liquids or gasses needs to be disinfected). Furthermore, in the present invention, a remote pulsed laser source is aligned to at least one optical fiber and the pulsed laser is operating in the wavelength range from about 230 nm (16a), to about 1064 nm (16b), and the pulses are distributed or delivered deep under ground (16c), through a guiding pipe (16d), or optical fiber thread pipe guide type (16e), or under sea (16f), or between rocky layers (16g) or any combination thereof (16h) using at least one optical fiber or a bundle of fibers (16i). The conduit or chamber (e.g. various disinfecting reactors) could have an elongated, or twisted, or curled, or bent shape. The conduit may run in parallel or in serial or combination thereof or be hydraulically or pneumatically shaped or any combination thereof for increasing or reducing flow rates of predetermined liquids or gasses, or for increasing or reducing the exposure time of said liquids or gasses to the pulses (17) or continuous (18) waves of light for irradiating or illuminating a predetermined volume of the liquids or gasses in the conduit or chamber where the fibers are distributed or supported. Such a conduit or chamber could be located within the drilling head (17a) or its filtration system or it could be positioned (or integrated into the drilling tower) before or after primary drilling has occurred or both.

A preferred embodiment is especially beneficial to the drilling industries for petroleum, or fresh water where clogging of filters in critical water (1), or petroleum (2), or liquids or gasses (2), or any combination thereof (2a), is substantially reduced resulting in less down time, less maintenance, and less periodical replacement in contradiction to the current technologies available in the drilling industries. Furthermore, the method of the present invention facilitates the use of available, reasonably priced, durable, pulsed laser light sources, such as a general type of high repetition, high peak power lasers, known from their wide use in telecommunication industries (for data transmissions applications).

In a preferred embodiment of the present invention, the conduit or chamber is an algae reactor having high industrial photosynthesis capabilities for CO2 fixation and/or utilization.

According to the method of the present invention, the disinfection is triggered by thresholds relating to levels of the liquid or gas flow rate or the predetermined disinfecting throughput efficiency required in according to geometry of the conduit or chamber types used. Furthermore, the present invention is especially beneficial where the optical fiber is incorporated in, or attached to, or oriented as light conducting surface disks, e.g. in filtration units designed to filter out particulate material above a predetermined size, or in backflash cleaning operation of existing water or air filters (e.g. filters for liquids or gasses utilizing surface disks, or membranes, or grids, or any combination thereof). The disks could have an appropriate refractive index profile for appropriate transmission throughout an interior of a predetermined conduit or chamber of predetermined geometry for simultaneously filtering and illuminating or irradiating a predetermined volume of liquids or gasses in the conduit or chamber.

BRIEF DESCRIPTION OF THE DRAWINGS

The present invention will be further described and illustrated in detail with reference to FIGS. 1–13. The following detailed descriptions of the preferred embodiment do not intend to limit the scope of the present invention in any way.

FIG. 1 illustrates a schematic layout of fibers in a conduit.

Figure 2:
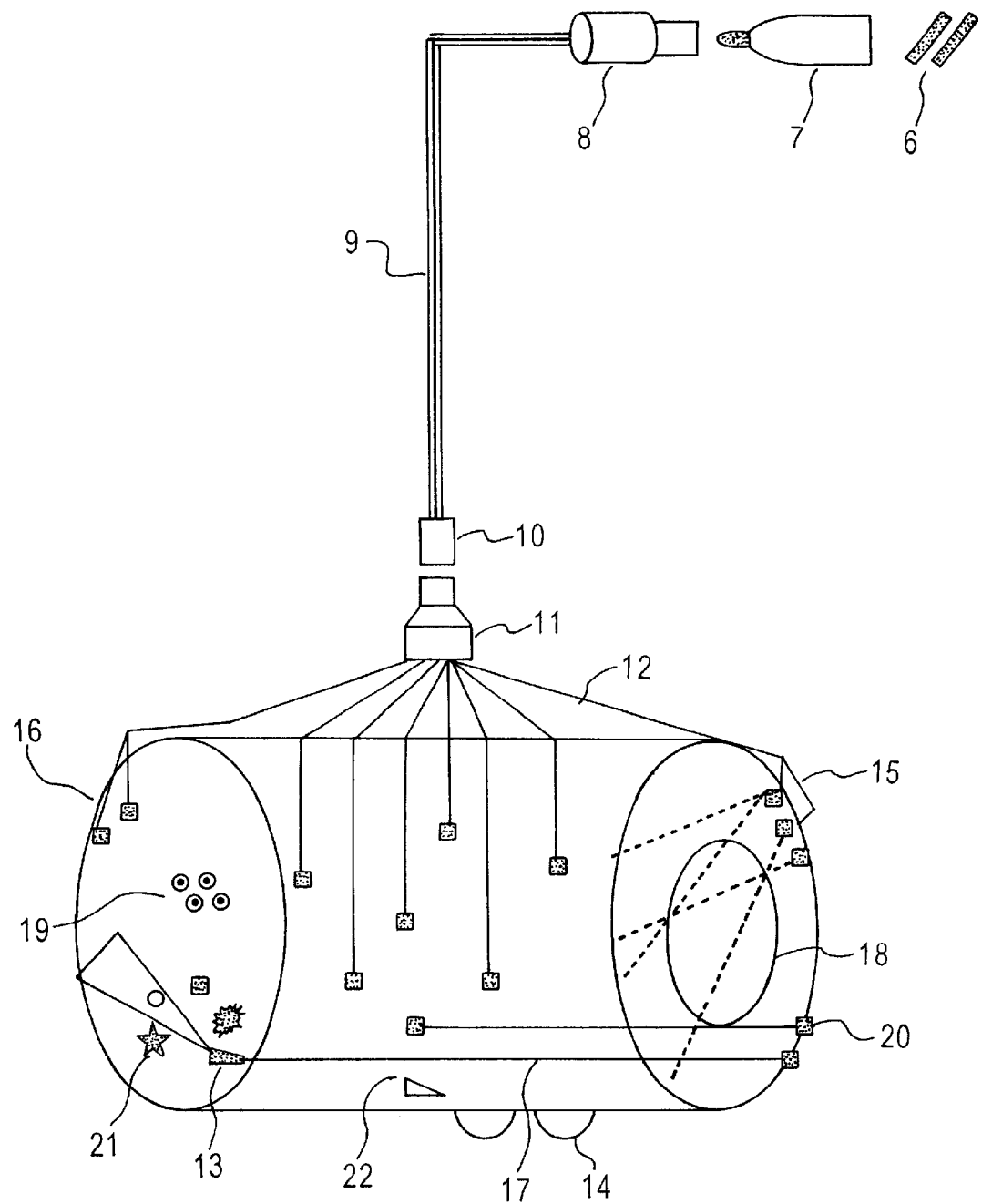
FIG. 2 illustrates a schematic layout of a semi holographic diffusive element in a conduit.

FIG. 2 illustrates a schematic layout of a semi holographic diffusive element in a conduit.

Figure 3:
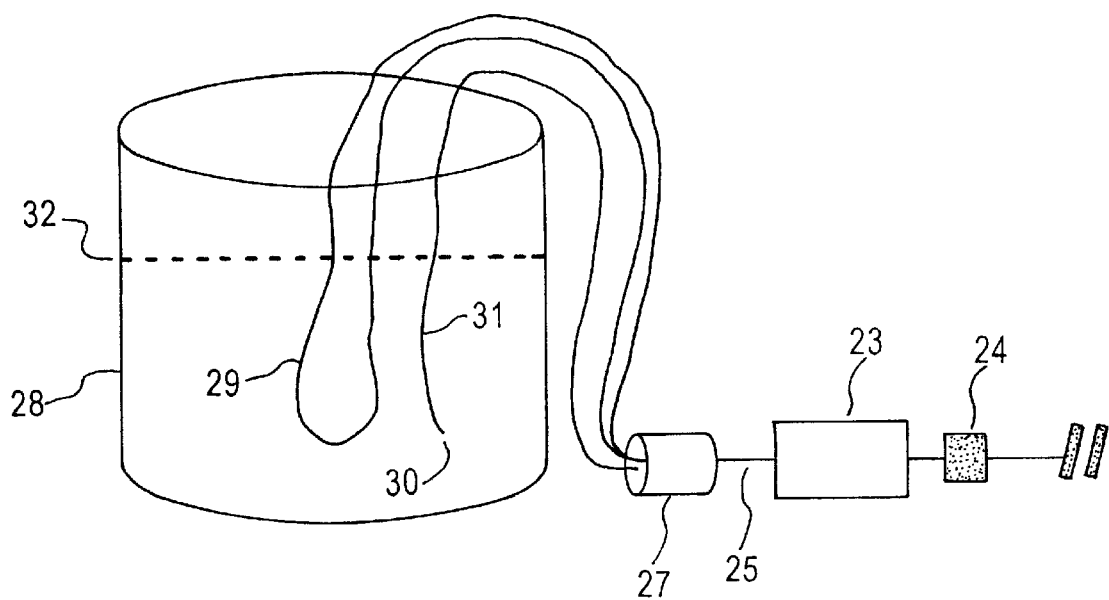
FIG. 3 illustrates a schematic layout of a combination of looped and end glowing fibers in a chamber.

FIG. 3 illustrates a schematic layout of a combination of looped and end glowing fibers in a chamber.

Figure 4:
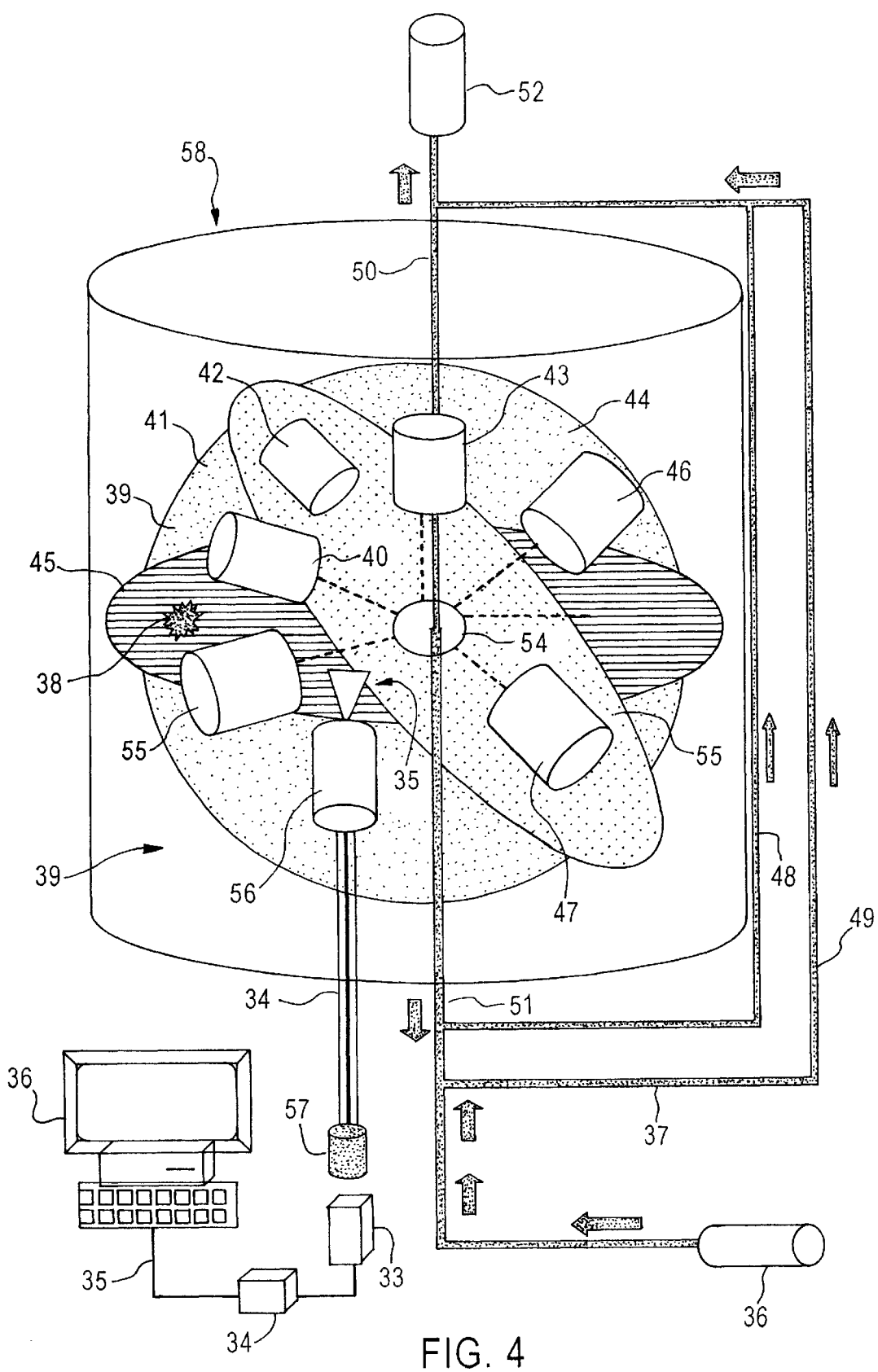
FIG. 4 illustrates a schematic layout of a multi tail optical cable assembly with a control and monitoring system.

FIG. 4 illustrates a schematic layout of a multi tail optical cable assembly with a control and monitoring system.

Figure 5:
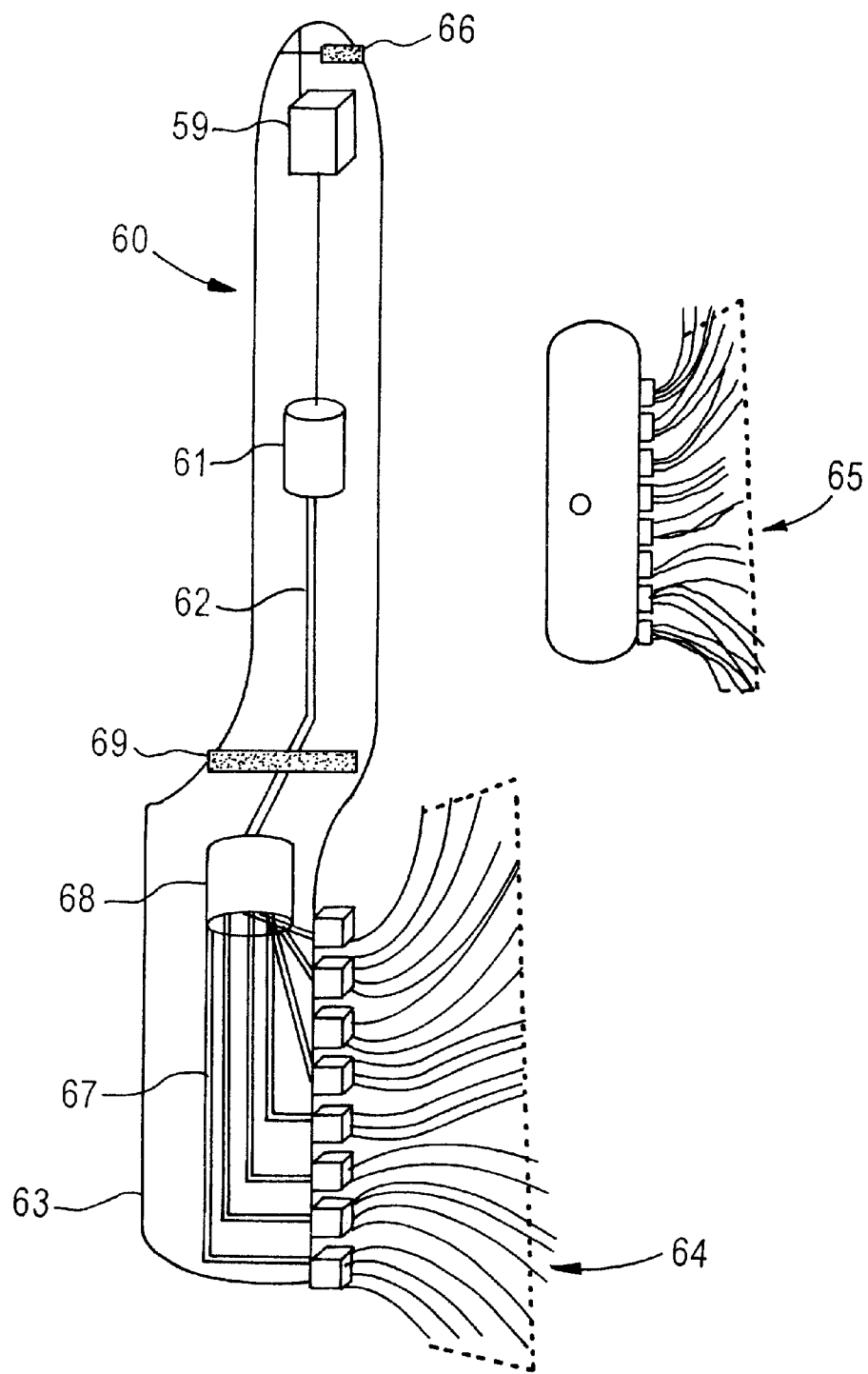
FIG. 5 illustrates a disinfecting brush (e.g. a toothbrush).

FIG. 5 illustrates a disinfecting brush (e.g. a toothbrush).

Figure 6:
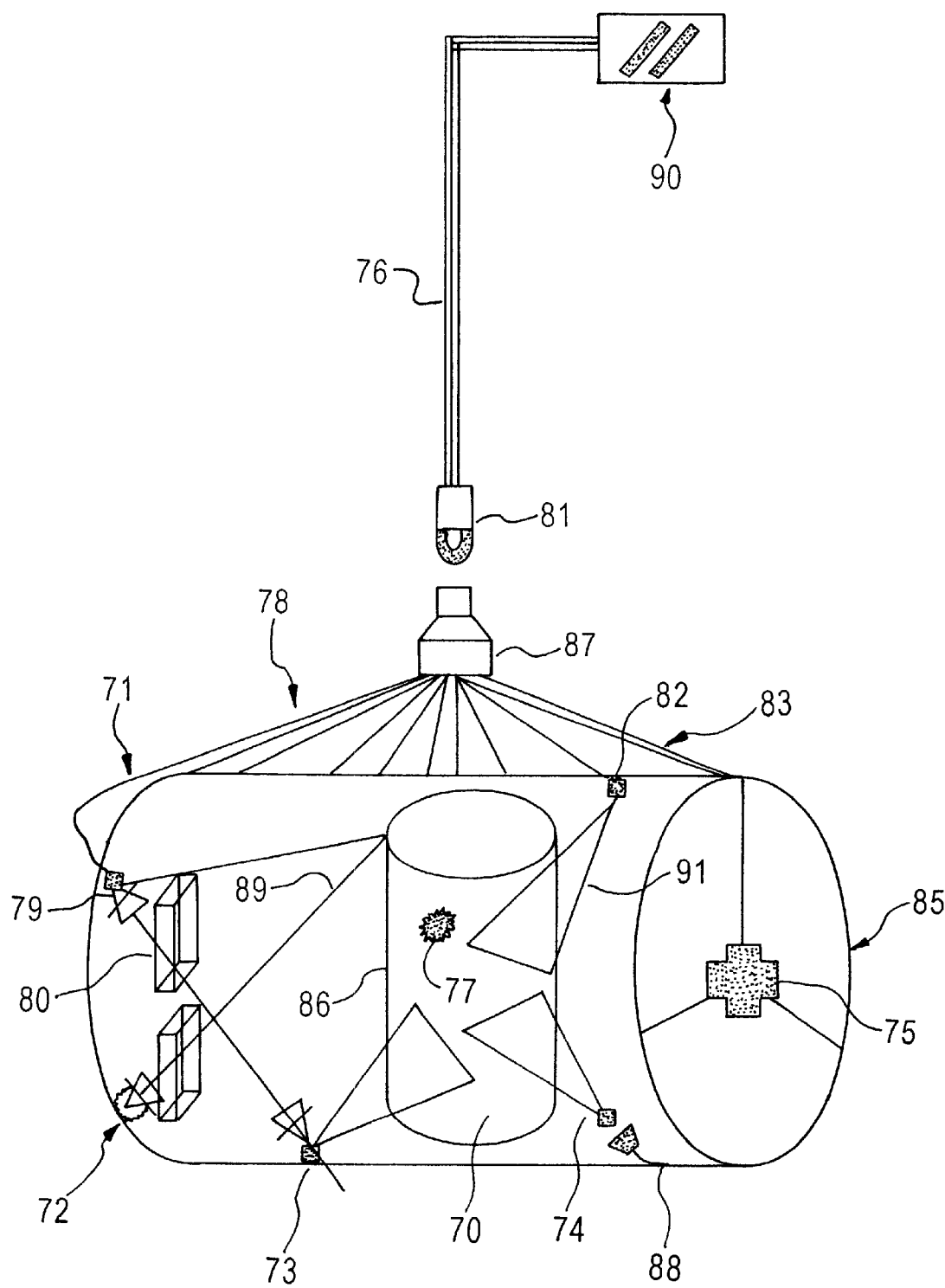
FIG. 6 illustrates a schematic view of variously oriented fibers in a conduit.

FIG. 6 illustrates a schematic view of variously oriented fibers in a conduit.

Figure 7:
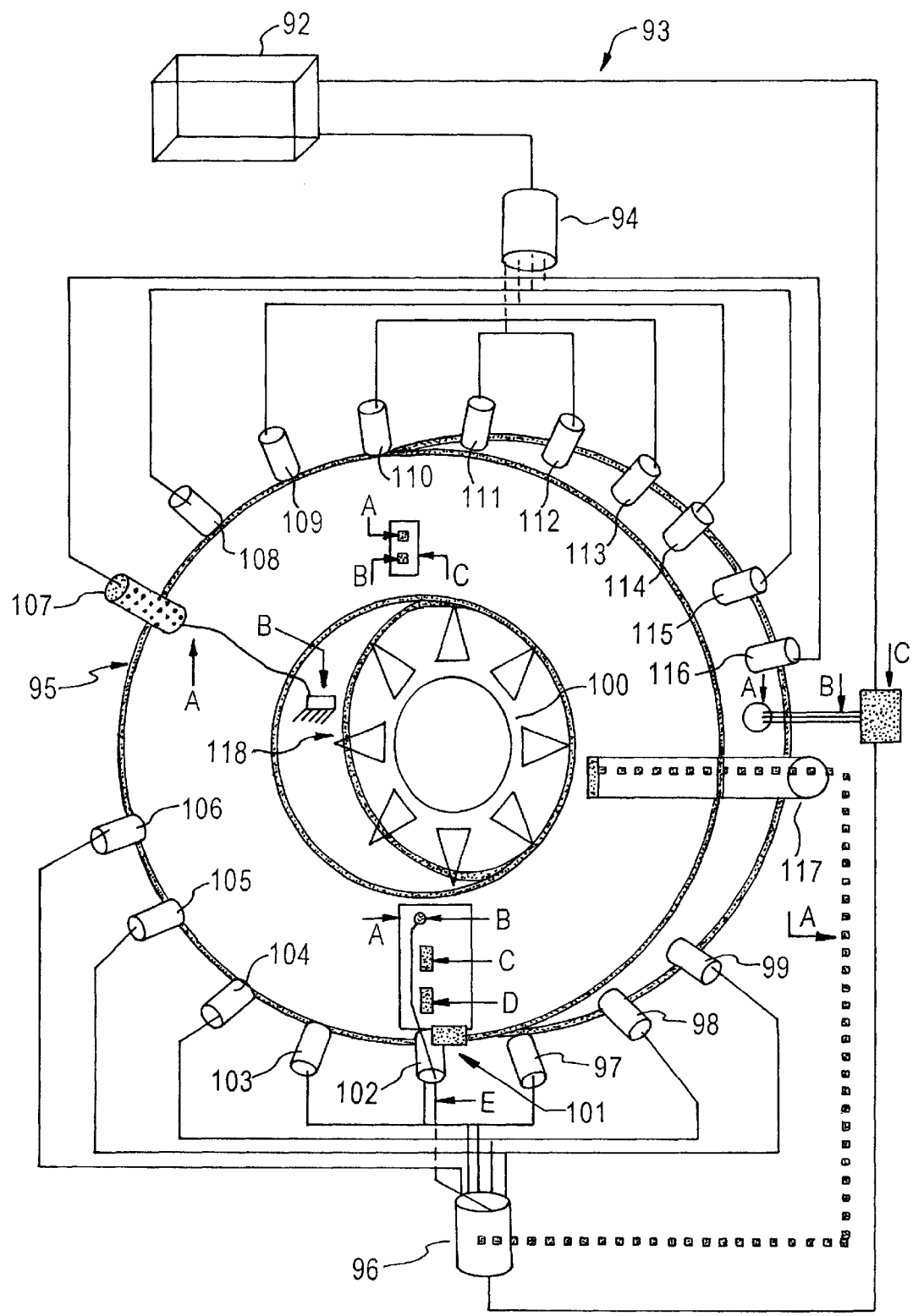
FIG. 7 illustrates a schematic view of a semi holographic, partially dielectric, harmonic ring with multiple delivery architecture.

FIG. 7 illustrates a schematic view of a semi holographic, partially dielectric, harmonic ring with multiple delivery architecture.

Figure 8:
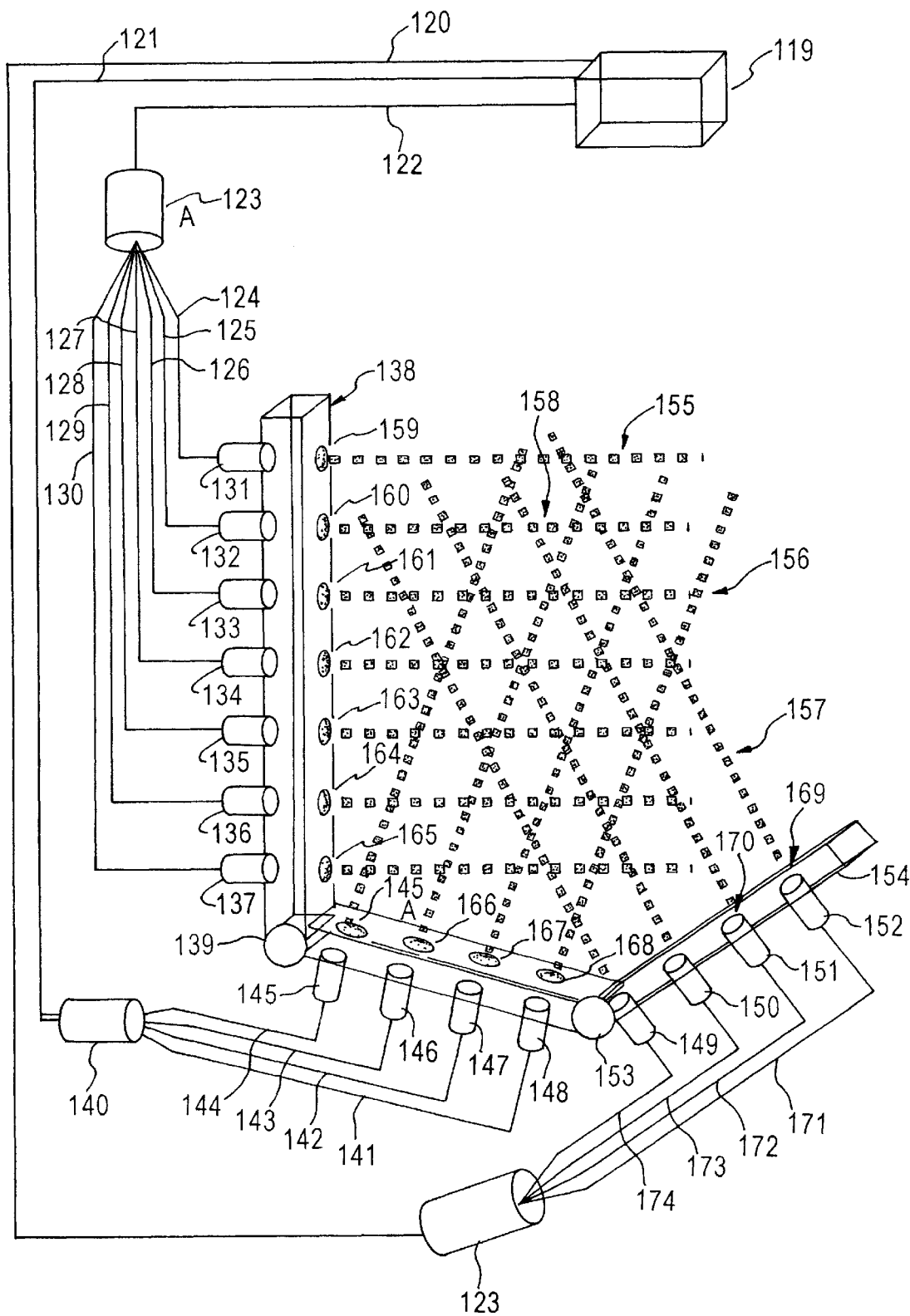
FIG. 8 illustrates a schematic view of a swiveling frame with a selection of fibers and crystals for harmonic generation of optical radiation.

FIG. 8 illustrates a schematic view of a swiveling frame with a selection of fibers and crystals for harmonic generation of optical radiation.

Figure 9:
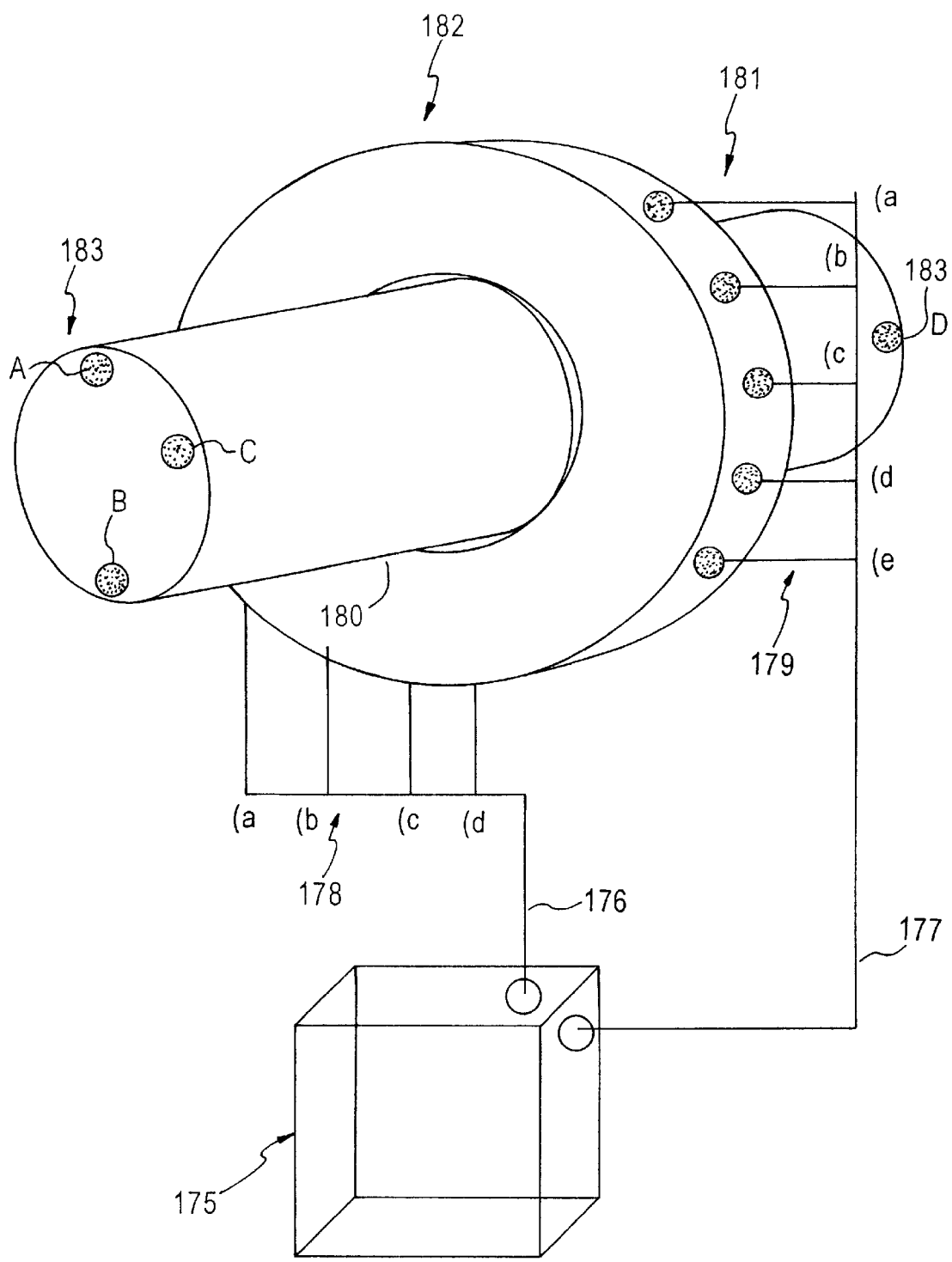
FIG. 9 illustrates a schematic view of a semi holographic ring featuring variable transparency conduit.

FIG. 9 illustrates a schematic view of a semi holographic ring featuring variable transparency conduit.

Figure 10:
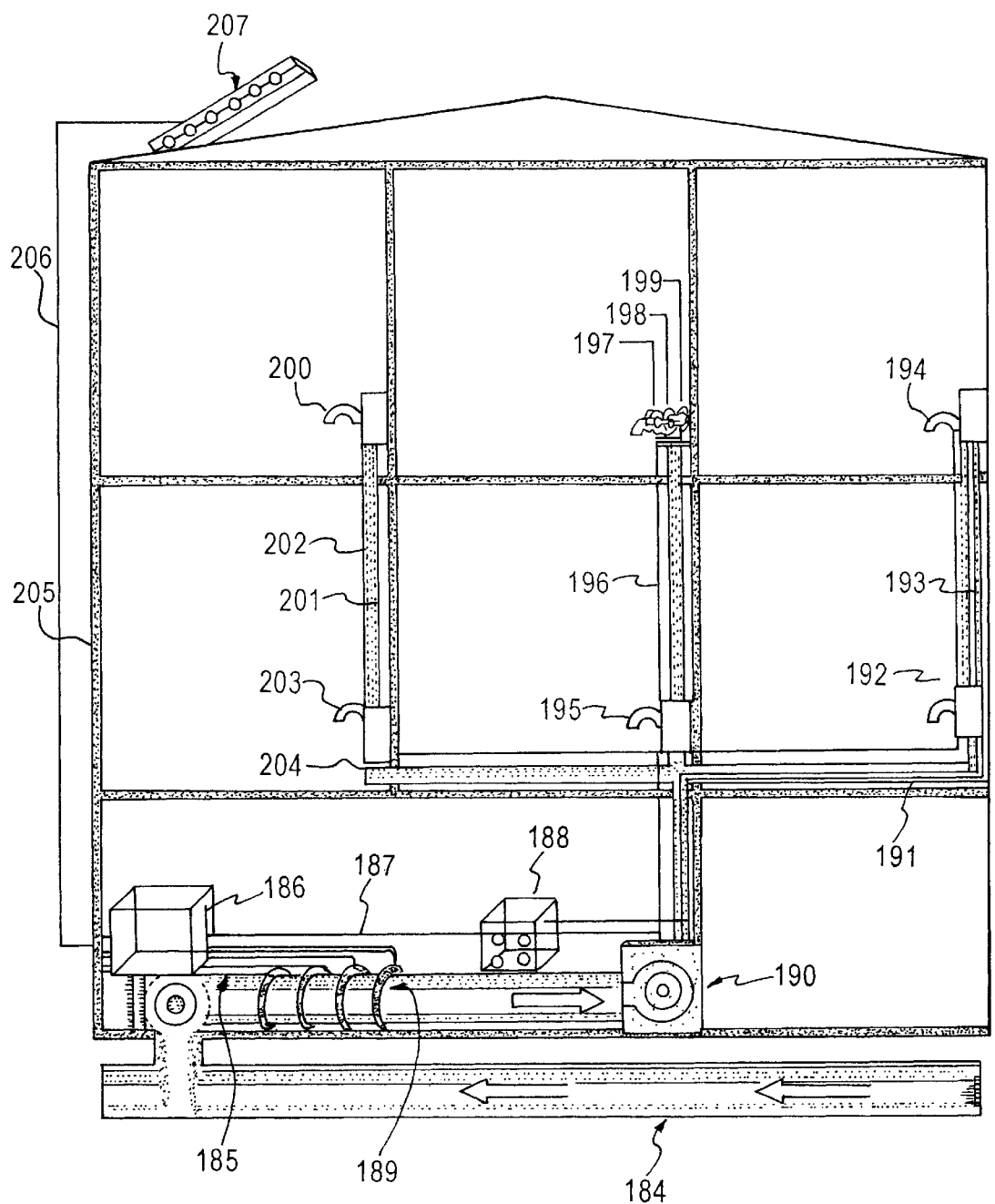
FIG. 10 illustrates a schematic layout of a municipal and domestic harmonic disinfecting network.

FIG. 10 illustrates a schematic layout of a municipal and domestic harmonic disinfecting network.

Figure 11:
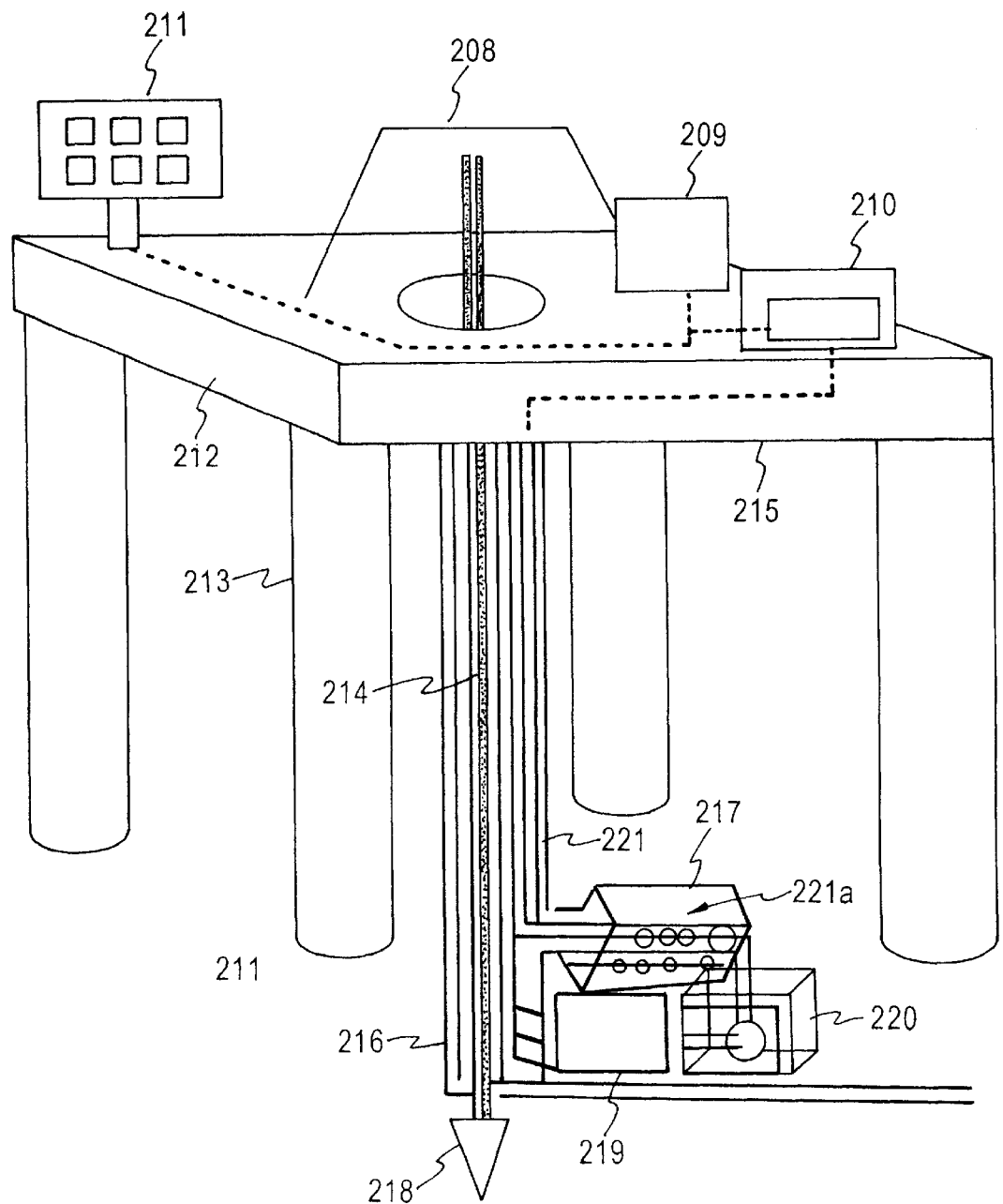
FIG. 11 illustrates a schematic view of a petroleum or fresh water well disinfecting system.

FIG. 11 illustrates a schematic view of a petroleum or fresh water well disinfecting system.

Figure 12:
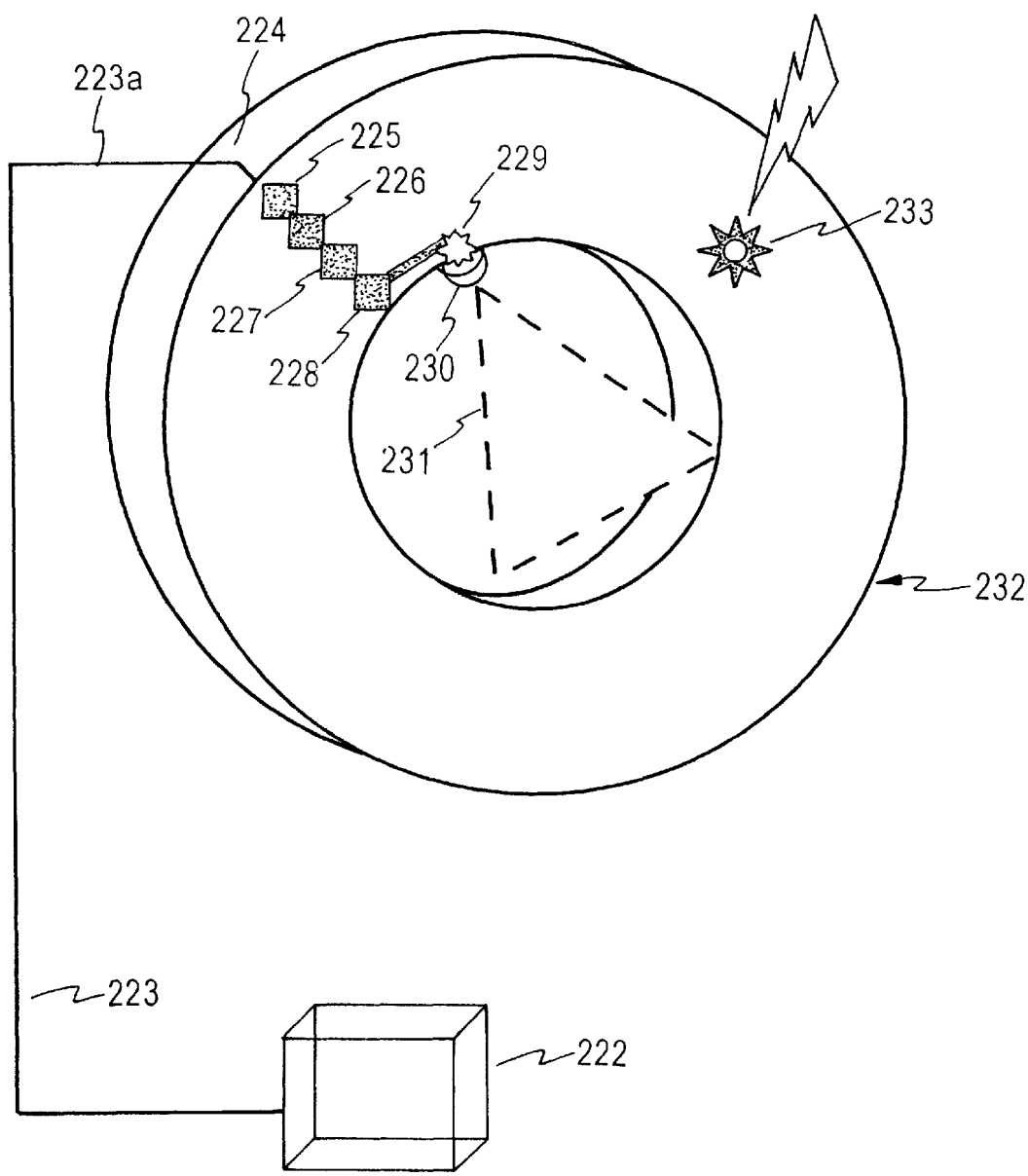
FIG. 12 illustrates a schematic view of a harmonic thermally isolated and stabilized semi holographic diffusive ring.

FIG. 12 illustrates a schematic view of a harmonic thermally isolated and stabilized semi holographic diffusive ring.

Figure 13:
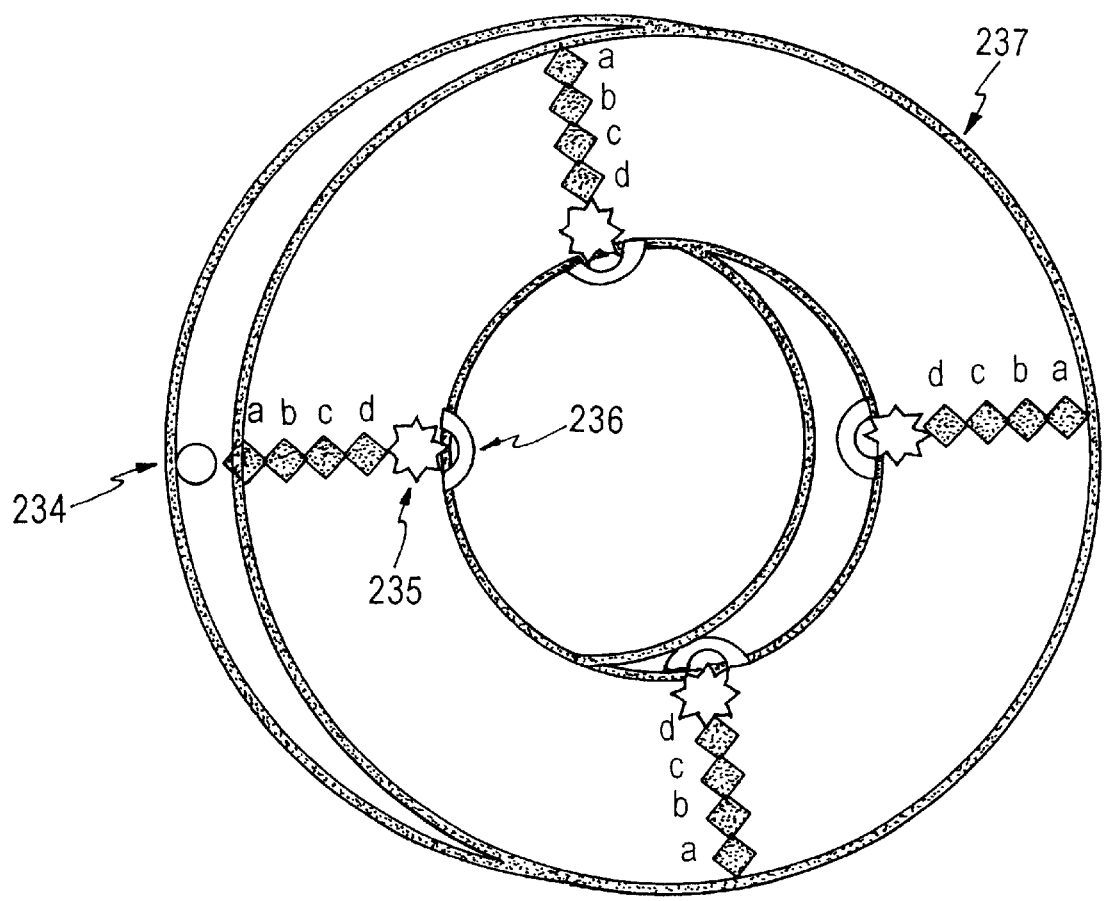
FIG. 13 illustrates a schematic view of a semi holographic, partially dielectric ring with crystal arrangement.

FIG. 13 illustrates a schematic view of a semi holographic, partially dielectric ring with crystal arrangement.

DETAILED DESCRIPTION OF THE INVENTION

FIG. 1 illustrate a schematic view of a device for disinfecting liquids or gases.

A device for disinfecting liquids or gasses is shown, comprising at least one optical fiber (1) located within a conduit (2) or a chamber, and a radiation unit having a high intensity source (3) of light. The light is coupled (4) the fiber, wherein the fiber is distributed within the conduit for illuminating a predetermined volume of liquids or gasses therein. A crystal reflective member (5) is shown with at least one region of constructive interference above it.

FIG. 2 illustrates a schematic view of another device for disinfecting liquids or gasses. A device for disinfecting liquids or gasses is shown, comprising at least one optical fiber (17) located within a conduit (14) or a chamber, and a radiation unit having a high intensity source (7) of light. The light is powered by an electrical power source (6) and launches with a primary wavelength from 399 nm to about 2800 nm, and coupled to a fiber harness connector (8). The light is transmitted through a light guide (9) wherein the light guide end portion (10) is connected to a central multi-tail optical fiber harness (11) from which the fibers are distributed within the conduit (14) or chamber for illuminating a pre-determined volume of liquids or gasses therein (with wave length of from about 180 nm to about 400 nm). A polarization maintaining optical fiber is illustrated on the left (16) extending to illuminate (with a wave length of 266 nm to 1064 nm) the inner space of the conduit or chamber. An additional solarization resistant optical fiber (12) is illustrated on the right to extend to surround the body of the conduit marked as illustrated by doted line on the left cross section of the conduit. This fiber crystal inter-mated end portion (13) is illustrated as projecting (irradiating or illuminating) harmonically generated, frequency doubled, or converted or any combination there of light beams of a wave length of from about 266 nm to about 1064 nm. The important attribution of particle size distribution (PSD) to light transmission (within the conduit or chamber) is demonstrated on the left by two particles (21) to demonstrate optimal (preferred) condition for light transmission within the conduit or chamber. The level of Total Suspended Solids (TSS) (19) contained in the predetermined volume of liquids or gasses shows its important attributions for light transmission efficiency (within the conduit or chamber). A crystal reflective member (22) as illustrated at the center of the conduit or chamber, reflects or absorbs the light from the fibers sides (12) and end portions (16) on the left and (15) on the right. Element 20 represents a liquid light guide (in addition to the optical fibers) distributed within the conduit or chamber and connected at the back to the central multi-tail harness (11). A constructive interference and/or diffusion (18) is shown on the right. A semi-holographic formation is formed by the radiation unit's primary wavelength or frequency of light (and projected from the fibers) and its secondary (e.g. $2^{nd}$, and/or $3^{rd}$, and/or $4^{th}$, harmonically generated, or frequency doubled, and/or converted) wave length in the Visible, and/or UVA, and/or UVB, and/or UVC regions or any spectral combination thereof which has a wave length of from about 218 nm to about 2400 nm.

FIG. 3 illustrates a schematic view of a device for disinfecting liquids or gasses.

A device for disinfecting liquids or gasses is shown, comprising at least one optical fiber (31) located within a conduit or a chamber (28) which could be scaled up to be a pond, a channel, container, large tanks, pipes, and/or subminiaturized for medical or surgical transplants, in dialysis, in medical preparation of complex compounds, in drinking water, or confined air. A radiation unit has a high intensity source (23) of light and is powered by an electric power (24) supply unit. The primary wavelengths or frequencies of light from UVA, and/or UVB, and/or UVC, and/or Visible, and/or NIR, and/or IR regions of the spectrum or any combination thereof from the radiation unit is coupled (27) to the fiber, wherein the fiber is distributed within the conduit or chamber for illuminating (with a wave length of 233 nm to about 532 nm) a predetermined volume (32) of liquids or gasses therein. The distribution of the fibers within the conduit or chamber are illustrated to include a single individual fiber distributed (31) and/or crystal terminated or intermated for direct projection and/or harmonic generation of secondary (e.g. $2^{nd}$ harmonic generation) from the primary wavelength and frequencies of light. A looped distributed bundle of side emitting optical fiber (29) is also shown within the conduit or chamber for illuminating and/or irradiating the liquids or gasses therein. e.g. with the secondary $2^{nd}$, and/or $3^{rd}$, and/or $4^{th}$ harmonically generated wavelength and/or frequencies of light.

FIG. 4 illustrates a schematic view of a device for disinfecting liquids or gasses.

A device for disinfecting liquids or gasses is shown, comprising at least one optical fiber (56) located within a conduit (58) or a chamber and a radiation unit having a high intensity source (33) of light controlled by a computer (36). The light is coupled (57) into the fiber, wherein the fiber is distributed within the conduit or chamber for illuminating or irradiating a predetermined volume of liquids or gasses therein. FIG. 4 illustrates an integrated filter wherein the device of the present invention is illustrated as a plurality of side emitting optical fibers, and/or end glowing fibers and/or PM (polarization maintaining) optical fibers as well as fractured fibers, and/or solarization resistant fibers (56) for guiding light of a wave length of from about 187 nm to about 400 nm (55), or from about 249 nm to about 279 nm (40), or from about 149 nm to about 290 nm (42), or from about 250 nm to 700 nm (43), or from about 180 nm to about 400 nm (46), or from about 400 nm to about 700 nm (47), or from 180 nm to about 2400 nm. The fibers are distributed within the conduit or chamber so that the fibers are distributed within or around a plurality of transparent light conducting or diffusing surface disks (45)(39)(44) designed to filter out particulate materials (38) in the liquids or gasses disinfected path (51). The filter is shown together with a recycling path marked with "R" (49 R) for the liquids or gasses to pass through. A pre-illumination filtering module (36) and a post-illumination filtering module (52) are included for getting an adequate level of particle size distribution (PSD) where the fibers are distributed within the conduit or chamber, for illuminating or irradiating the liquids or gasses and/or receiving light for remote feedback control of primary and/or secondary wavelengths or frequencies of light. The device of the invention allows for maximizing fiber transmission efficiencies and/or damage thresholds or physical or optical tolerances (by e.g. using IR 1064 nm as primary light to be coupled to the fiber and/or converted up or down, and/or frequency doubled). The invention uses either direct (e.g. end-to-end) fiber transmission, and/or $2^{nd}$, and/or $3^{rd}$, and/or $4^{th}$ harmonic generation obtained by nonlinear crystals or other means for harmonic generation between the radiation unit and the fibers receptive $1^{st}$ end termination, or between the radiation unit and the projective crystal or isolating lens (54, 56) at the $2^{nd}$ end termination of the fiber.

FIG. 5 illustrates a schematic view of a device for disinfecting liquids or gasses.

A device for disinfecting liquids or gasses is shown, comprising at least one side emitting optical fiber (62) located within a conduit (67) or a chamber and a radiation unit (60) having a high intensity source of primary light frequencies wherein the light is powered by batteries (59). The light is coupled to the fibers, wherein the fibers are distributed and interfaced with, or having integral or intermated crystals as reflective end cups (68) for directly projecting, and/or for obtaining $2^{nd}$, and/or $3^{rd}$, and/or $4^{th}$ harmonically generated frequencies of light within the conduit (64) or chamber for illuminating or irradiating a predetermined volume of liquids or gasses therein. A spare head (65) is shown at the bottom of the figure to indicate that it can be replaced (e.g. together with crystal) for continuous use by dismantling or disconnecting (69) the device.

FIG. 6 illustrates a schematic view of a device for disinfecting liquids or gasses.

A device for disinfecting liquids or gasses is shown comprising at least one region of constructive interference (70) generated from a holographic element (80) which is attached to the frame (enclosure) of a conduit (85) or a chamber, for eliminating head loss within the conduit or chamber which is positioned opposite a reflective member (at the top left corner) (79), bottom left corner (72) top left (82), bottom right (74), top (89), top (82). A solid particle (77) is illustrated to show its important attribution to light transmission within the liquids or gasses to be disinfected. The radiation unit has a high intensity source (81) of (coherent) light of a wave length of from about 200 nm to about 700 nm. The radiation unit is powered by an electrical power supply unit (90). The coherent light from the radiation unit is coupled (87) to at least one (side emitting) optical fiber (shown at left top corner) (71), bottom right corner (88) surrounding the body of the conduit (85) or chamber.

Element (75) represents a secured opening on the far right hand side (a secured lid or cover). FIG. 6 illustrates a conduit or a chamber wherein (a hologram is formed) out of at least one region of constructive interference created by light beams (of axis or reference beams) (91). FIG. 6 illustrates coherent light from the radiation unit (81) is coupled to a multi tail harness (87). The light gets carried by the fiber (71) to a reflectance member (79) and gets projected through the holographic element (80) positioned directly in front of the reflective member. At least one side emitting optical fiber is distributed within the conduit or chamber for illuminating (91) (86) or irradiating a predetermined volume of liquids or gasses therein.

FIG. 7 illustrates a schematic view of the device for disinfecting liquids and gasses. A device for disinfecting liquids and gasses is shown, comprising at least one optical fiber (93) distributed in the region (18) to be disinfected; The radiation unit (92) has a high intensity source of primary light of a wave length of from about 218 nm to about 1064 nm to be coupled to the fibers. The liquids or gasses are radiated by the optical fiber over a predetermined period of time. Element (94) represents a multi-fiber assembly splitting the single beam to 10 individual split independent feeds (107, to 116) thereby broadening the range of disinfecting reactor geometry which can be used by producers and/or end users who currently do not have efficient means to split optical radiation for the purpose of disinfecting liquids and gasses. The present invention is not so limited and can be used for splitting and transmitting and radiating and/or delivering or diffusing, or projecting light from the fibers. Unlike previous methods which bring the water (e.g. liquids and/or gasses) to the light, the present invention brings the light to the liquids and gasses. Each feed extends to the ring through fibers for delivering a primary wavelength (e.g. 1064 nm in the IR region and/or 266 nm in the UVB region), via a semi holographic (100), (118), diffusive, partially dielectric ring support means (95), from the radiation unit to 10 of the ring's inputs, and/or outputs (107–116) e.g. in and/or out of the conduit or chamber, which for the purpose of the present invention could be transparent, or translucent, or semi opaque. The conduit or chamber may have diffusive properties suitable for diffusing optical radiation and/or an adequate refractive index profile for conducting light through (e.g. simultaneously guiding light by total internal reflection and the liquids and gasses hydraulically by pressure). For the purpose of disinfecting, light is projected from outside the transparent conduit or chamber where the fibers are distributed. The fibers are used in bi-directional transfer mode wherein each (108), (109), (110), (111), (112), (113), (114), (115), (116), of the individual fiber bundles extends substantially to a predetermined distance from the radiation unit and terminating, and/or inter-mating to at least one thermally isolated and/or stabilized modular harmonizing crystal interface (such as KTP and/or PPKTP and/or LBO crystals, or equivalent electro-optical conversion means for generating $2^{nd}$, and/or $3^{rd}$, and/or $4^{th}$, and/or $5^{th}$ harmonics). A plurality of non linear crystals are selected and sequentially positioned (108–116) e.g. inside a plurality (not shown) of wavelength specific crystal equipped cartridges (101) wherein the cartridges containing the crystals are thermally isolated (C). Temperature stabilization sensing means (A) and an additional optical fiber (B) are interconnected to the same network extension feed or multi tail fiber assembly for carrying signals to a controller (96), (94), such as multi-tail fiber harnesses. The crystals, indicated at (D) and (E), are secured at a predetermined angle or phase and at a predetermined distance from the sensing means (A). The ring's input/outputs are set to receive primary optical radiation from the radiation unit wherein the fibers are aligned to the radiation unit. The optical fibers are interfaced, or inter-mated or integrated (102), (103), (104), (105), (106), to additional fiber inputs leading to additional cartridges (not shown) wherein the optical radiation is delivered unchanged (e.g. without wavelength change) for direct spectral transmission from the radiation unit. So, the same ring support means delivers optical radiation to the liquids or gasses flowing throughout its optically covered (100), (118) inner dimension. A plurality of wavelengths (e.g. both direct or harmonically generated or frequency doubled such as SHG, THG, FHG) are delivered by the fibers for radiating a predetermined volume of the liquids and gasses with the light from the fibers. Element (107) is polymethyl(phenyl) siloxan based transparent diffusive tips grouped together (107 B) in a shape of a brush and extending substantially into the liquids and gasses to be disinfected. The brush is optically interfaced to a diode type laser (or a bar of diodes) positioned sequentially, substituting fiber input (107) (shown in bold) and excepting its primary pumping wavelengths of from about 400 nm to about 670 nm from the radiation unit (92) via the optical fiber feeds extending from fiber assembly (94) to the diode laser. Element (A) represents a shorter segment of fiber which feeds radiation to the siloxan based brush tips. Adequate contact and/or exposure to the liquids and gasses passing through the ring is maximized. The diffusive tips further reduce headloss and help maximizing effective inactivation of noxious microorganism or noxious bacteria and/or microorganism in the liquids and gasses to be disinfected. Element (116 A) is illustrating a temperature isolation and stabilization sensing means, connected through (B) to the radiation unit (94). An optical junction is shown at (C) interconnecting and encapsulating both the main multi-tail optical cable assembly (93) and the sensor connecting fiber (B) together for easy integration to a wide variety of environments or site topographies. Element (117) is an empty fiber insert point for carrying optical radiation via the optical fibers to a remote control and data acquisition unit (not shown) for feedback control of relevant parameters of the system. Element (117 A) shown as a doted line denotes the path along which the additional fiber needs to be connected to the fiber insert (fiber not shown). Element (110) is a crystal cartridge having two individual crystals (B), (A), (the crystals are aligned and phase—matched to the fiber's $2^{nd}$ end termination (not shown) and are thermally stabilized and or isolated.

FIG. 8 illustrates a schematic view of the device for disinfecting liquids or gasses. A device for disinfecting liquids and gasses is shown, comprising at least one optical fiber (120), (124), (125), (126), (127), (128), (129), (130), (142), (143), (144), (171), (172), (173), (174), or a bundle of fibers (122), (121) distributed in the region to be disinfected (158), (156), (155), (157). At least one radiation source having a high intensity source of light (119), is coupled to the fibers (alignment not shown). The liquids and gasses are radiated by the fibers over a predetermined period of time. Elements (131 to 137) represent fiber inputs each having means for transmitting identical or down converted optical radiation at predetermined wavelength and frequency. Elements (139), and (153) illustrate pins allowing the entire frame to adjust to a wide variety of geometry. Elements (159 to 165) represent elastic or durable lenses each having a predetermined divergence so as to collectively fill in the inner space of the frame (154). Additional transparent elastomer based lenses (such as polydimethylmethilsiloxan) are illustrated at (145), (166), (167), (168) each having a different divergence or focus for the purpose of radiating a predetermined volume of the liquids and gasses through the frame. Fiber inputs (151), (152), (150), (149), (153), deliver optical radiation of a wavelength of from about 180 nm to about 2600 nm wherein the primary wavelength from the radiation unit is converted at least once into SHG, and/or THG, and/or FHG, and/or any spectral combination thereof by e.g. $2^{nd}$, $3^{rd}$, $4^{th}$, harmonic generation using thermally isolated or stabilized crystal cartridges (not shown). Element (138) illustrates additional swiveling frame support means. Element (146), (147), (148) illustrate individual fiber feeds (142–144) extending from the fiber assembly (140), wherein the primary wavelength of a wavelength of from about 140 nm to about 2600 nm is delivered and/or converted and/or diffused into the liquids and gasses through the frame.

FIG. 9 illustrates a schematic view of the device for disinfecting liquids or gasses. A device for disinfecting liquids or gasses is shown comprising at least one optical fiber (181), (179), (176), (177a, b, c, d, e,), (178a, b, c, d,) distributed in the region to be disinfected. At least one radiation unit having a high intensity source of light (175) is coupled to the fibers. The liquids and gasses are radiated by the optical fibers over a predetermined period of time. A semi holographic, partially dielectric, thermally isolated or stabilized ring (182) is coupled (e.g. by quick coupling) to form a continuing conduit (the conduit could be transparent, or opaque, or translucent, or have a predetermined refractive index profile for guiding light in accordance with conditions for total internal reflection) at each side. Elements (183) and (183a, b, c) illustrate sequentially positioned fiber inputs (a, b, c) wherein (183d) is positioned at the other side of the ring for alternating delivery of optical radiation of a specific spectral distribution between cross sectional radiation from the ring (182), and the longitudinal projection (183a, b, c,) of the fiber inputs (183a, b, c, d). Parameters associated with the liquids or gasses to be disinfected (such as turbidity, or transparency or levels of suspended solids in water or air) provide thresholds for feedback control and/or triggering of the radiation unit and/or control unit (not shown).

FIG. 10 illustrates a schematic view of the network for disinfecting liquids or gasses. A network for disinfecting liquids and gasses is shown comprising at least one optical fiber (185), (187), (191), (193), (201) distributed in the region containing the liquids and gasses to be disinfected. At least one radiation unit having a high intensity source of light (186) is coupled to the fibers. The liquids and gasses are radiated by the optical fiber over a predetermined period of time. An interactive optical infrastructure network for disinfecting the liquids and gasses comprises, in the region of the liquids and gasses to be disinfected, at least one optical fiber (196), 191 having a receptive $1^{st}$ end termination, and a $2^{nd}$ end extending substantially into the conduit or chamber, and inter-mated on entry at a predetermined angle, to a at least one modular 2nd, and/or $3^{rd}$, and/or $4^{th}$, harmonic generation crystal module interface (197), (198), (199), (189). The crystal is terminated with an isolating transparent lens (not shown) or diffusing tips (not shown) facing the liquids and gasses to be disinfected. At least one radiation unit (186), having a high intensity source of light is coupled to the fibers. Via receptive vacuum, or thermally protective interface (188), the fibers 1st end termination (not shown) receives high intensity light having a primary wavelength in the Visible, and/or NIR, and/or IR, and/or UV (UVA, UVB, UVC) regions of the spectrum. The light Illuminates or irradiates (199, 198, 197,) a predetermined volume of the liquids and gasses wherein the delivered light has identical, or secondary, or tertiary wavelength ranges in the UVA, and/or UVB, and/or UVC, and or Visible, and/or IR regions of the electromagnetic spectrum, or any harmonically generated, or converted spectral combination thereof. Element (204) illustrate infrastructure support means (204) for distributive the fibers substantially to cover a large area (unlike previous methods and means) using a single light source. Elements (203), (200), (195), (194), (192), represent end user points of use (such as a tap, or a network of pipe extensions). Element (190) illustrates a central pump (with an arrow facing the pump for clear indication of the liquid and gas direction of flow) for distributing the liquids and gasses throughout the house or building (205). The liquids/gasses arrive from a lower main liquid and gas supply line (marked with two arrows pointing left). Rooms in a house on different floors are illustrated to further show splitting and delivery (for covering large areas) or diffusion of light by the optical fiber network extending for substantial distance. A solar panel is illustrated at (207) to be placed on the roof of the building or house for powering the radiation unit (185).

FIG. 11 illustrates a device for disinfecting liquids and gasses. A device for disinfecting liquids and gasses in wells and drilling sites comprises at least one optical fiber (215), (221), (216), (214) distributed in the region containing the liquids or gasses to be disinfected. At least one radiation unit (210) having a high intensity source of light is coupled to the fibers. The liquids or gasses are radiated by the optical fibers over a predetermined period of time. FIG. 11 illustrates the ability of the device of the present invention to disinfect liquids or gasses (e.g. found in petroleum and/or fresh water drilling sites and wells, both, under the sea and under ground) where drilling installation requires a solution to clogging (clogging of water filters for cooling systems to the drilling heads and/or ground water which is contaminated). The present invention, by delivering radiation using optical fibers, can provide an easy solution to the clogging problem thereby enhancing productivity and saving time and expenditure caused by maintenance and/or expensive periodical replacement procedures.

FIG. 12 illustrates a device for disinfecting liquids or gasses. A device for disinfecting liquids or gasses comprises at least one optical fiber (223), (223a), (224) distributed in the region containing the liquids or gasses to be disinfected. At least one radiation source (222), having a high intensity source of light is coupled to the fibers. The liquids or gasses are radiated by the optical fibers over a predetermined period of time. Elements (225), (226), (228), (227), represent a crystal arrangement (e.g. a cartridge) through which a primary wavelength from the radiation source of from about 160 nm to about 2600 nm is transmitted, and/or delivered without changes, and/or harmonically generated or frequency doubled, and/or up or down converted according to species specific disinfecting calibration standards. A transparent elastomeric lens (230) isolates the liquids or gasses from the inner surface of the crystals. The crystals are thermally isolated and/or stabilized (not shown) in a cartridge. The crystals are arranged in a semi holographic, dielectric ring (230), wherein the fibers reach and are inserted into the ring (one fiber is shown to reach the ring) (223) for delivering optical radiation of a predetermined spectral distribution. Element (233) illustrates the divergence effect of the isolating lens wherein the beams coming out of the lens (e.g. after passing through the crystal) is identical to the primary wavelength and frequency of light from the radiation unit (222). Alternatively, the light from the radiation unit could be converted into SHG, THG, FHG (e.g. by $2^{nd}$, and/or $3^{rd}$, and/or $4^{th}$ harmonic generation and/or frequency doubling) for converting the primary wavelength from about 1064 nm to about 532 nm, or from 532mn to about 266 nm (depending on the selected crystals in the cartridge (not shown). Light is projected with a predetermined divergence (231) for filling the inner space of the ring. An electric pulsed DC/AC input to the partially dielectric ring, shown at (233), lowers the impact of colloidal deposits and/or hard water deposits by contradicting the polarity and/or magnetic field of suspended organic solids in the liquids or gasses to be disinfected.

FIG. 13 illustrates a device for disinfecting liquids or gasses. A device for disinfecting liquids or gasses comprises at least one optical fiber (not shown) distributed in the region containing the liquids or gasses to be disinfected, one optical fiber input is illustrated at (234). At least one radiation unit (not shown) having a high intensity source of light is coupled to the fibers. The liquids or gasses are radiated by the optical fibers over a predetermined period of time. The crystals (a), (b), (c), (d) are arranged in a thermally stabilized or isolated cartridge (not shown). The crystals receive optical radiation from the radiation unit at a primary wavelength from about 200 nm to about 2400 nm wherein the crystals (such as KTP and/or PPKTP type or equivalent) convert the primary wavelength to a lower wavelength (such as a 532 nm and/or 266 nm) in the Visible and/or UVA, UVB, UVC regions of the spectrum. A transparent lens, illustrated at (236), isolates the liquids or gasses to be disinfected from the crystal cartridge. The ring is also thermally stabilized or isolated for maintaining and/or maximizing the conversion efficiency of the crystals.

EXPERIMENTAL EXAMPLES

The experiment was held at the department of Physical Chemistry laboratories at the Hebrew University in Jerusalem. Sigma Chemicals Israel Company have supplied 20 liter of the E-Coli fermented culture. Biological solutions and patric dishes were prepared.

Each stage of the experiment included two separate modes of Electro-magnetic radiation:
a. Pulse laser at a repetition rate of 10 Hz. Wavelength rated 93% at 266 nm and 7% at 532 nm.
b. Polychromatic continuous wave UV lamp with a broad bend (100 nm) centered at 300 nm.

Equipment

Laser setup includes a Nd/yag laser made by Spectra Physics and of a Quanta ray model Nd/yag DCR with Spectra A-702 2nd and 4th harmonic generation modules, which are computer controlled. The wavelength of the laser radiation as measured is 266 nm (93% at 266 nm, 7% at 532 nm). The pulse duration is 10 ns. The pulse power as measured is (Fiber delivery runs) 4 mJ per pulse at the end of the fiber. In direct irradiation (without the optical fiber) the pulse power is measured at 70 mJ (before entering the liquid).

Optical Signal Path
(a) Laser head, (b) $1^{st}$ steering mirror, (c) 2nd steering mirror, (d) 3rd steering mirror, (e) 1st focusing lens such as Oriel FO-315, (f) 2nd collimating lens such as Oriel CO-318, (g) Directive prism (90 degrees at 80% efficiency) (e) fiber.

Measuring Devices

"Offir Optronics" power meter, Scientec model 364— laser power meter (1 mj–2 joule)

The fiber types used throughout the experiment:
HGFS (high-grade fused silica) optical fiber bundle (manufactured by Oriel), Bi-furcated of 10 mm in total physical diameter for each arm, (2.5–3 mm NOD) HGFS total Bi-furcated bundle of 1 meter in length, bundle having a PVC/polyamide type sheathing which is opaque and comprises metallic reinforcing member.

A SiO2 (Homogenize Glass) fiber bundle, Atlantium type, at 8 mm in diameter comprises 5000 individual 50-micron fiber strands. Flat transmission at UVA spectrum. Total length of the bundle 3-Meter (originally a loop of 1.5 Meter out, 1.5 Meter in) fiber N/As is less than 0.7, nominal. No sheathing.

The components in the biological set up are:
Stainless steel sealed container, Ø170 mm, pierced with two fibers bundles for irradiation protection. SiO2 (crown glass) 1 liter Ø100 mm (large diameter dish), Magnetic stirrer base, Wild type of E.coli K12 strain 20 liter (for adequate sampling), Patric dishes with Seline (biological solution) for seeding.

The Experiment Setup

The laser head was positioned 5 meters from irradiation target (wild type of E.coli in 1 liter of water). The lenses to steer and direct the laser pulsed beam across the room were located above a tabletop surface. Mounting devices were used for holding a prism to direct the light beam down at a 90-degree angle.

The fiber bundles were aligned to the laser and connected in front of the prism preceding dual lens configuration for minimizing losses.

Surface losses in the optical chain: $1^{st}$, $2^{nd}$, $3^{rd}$ steering mirrors; $1^{st}$, $2^{nd}$ focusing lenses; prism surfaces loss; Each pulsing surface loses approx. 4% of total optical power output available at the next surface A total surface loss is of approx. 27% at output. Radiation through a distance of 6 meters of air should be accounted for additional 3% loss.

Polychromatic lamp setup—Oriel UV Xenon lamp XU-450 rated Power 450 W, equipped filters, lenses, attachments. 50 mW CW is measured at each end of HGFS bi-furcated fiber bundle. Attached filters were used for separating deep UV radiation at output. The lenses used were Collimator lenses, Paralleling beam lenses with spectral range 60% of irradiation at UV-VIS, enhanced at between 220 nm through to 325 nm respectively, a filter 7-54 centered at 300 nm.

Experiment Description

The Laser phase of the experiment included three modes of irradiation:
a) LD (large dish)/Loop (where both side of the loop are connected into one end termination)—Irradiation/radiation SiO2 side emitting fiber bundle s (5000 50 micron fibers) are aligned into the laser beam sheathing of one meter of the bundle was stripped off and distributed in the experiment dish. The dish was exposed to external light during the irradiation.
b) LD/O.F—Irradiation/radiation into HGFS, end-glowing, bi-furcated fiber bundle of 1 meter long aligned in to the laser beam. The end-glowing terminals were inserted through angle-adjustable holes in the stainless steel container cover. The container was sealed during the ration.
c) LD/Direct—the UV was irradiated/radiated directly (not through the optical fibers) into the dish via the prism.

The UV CW lamp phase—a Xenon lamp 450-Watt nominal UV—the irradiation was channeled into a HGFS, end-glowing, bi-furcated fiber bundle 1 meter long aligned into the laser beam. The end-glowing terminals were inserted through angle-adjustable holes in the stainless steel container cover. The container was sealed during the irradiation.

In both phases—exposure time was 600 sec (10 minutes) wherein periodical samples were extracted using pipette driven disposable tips. A solution was prepared for counting the culture during the next 24 hours.

Summary—POC results (e.g. proof of concept experiment results)

Counting of developed cultures of E.coli, wld type, 24 hours later. The results were summarized in the following table:

| EXPOSURE DURATION | PULSE LASER IRRADIATION | | | LAMP |
|---|---|---|---|---|
| | LD/Loop (a) | LD/O.F (b) | LD/Direct (c) | LD/O.F |
| 2 Seconds | 0 | 0 | 12 | 38 |
| 10 Seconds | 0 | 0 | 2 | 14 |
| 30 Seconds | 0 | 0 | 1 | 23 |
| 60 Seconds | 0 | 0 | 0 | 7 |
| 180 Seconds | 0 | 0 | 0 | |
| 300 Seconds | 0 | 0 | 0 | |
| 400 Seconds | | | | 7 |
| 600 Seconds | 0 | 0 | 0 | 4 |
| REFERENCE (24 hours - no irradiation) | 49 | 42 | 47 | 45 |

The results as shown in the table indicate that very fast disinfection (less than 2 seconds) was achieved by using the side emitting fiber (mode a) and end-glowing fiber (mode b) while direct irradiation/radiation (mode c) showed total disinfection only after 1 minute. Reference results using UV lamp through fiber appeared to show much slower disinfection (total disinfection was not achieved). The UV lamp results correspond to the known characteristics in the existing literature.

Contrary to the existing technology, frequently backed by researchers in the relevant environmental fields and contrary to the existing knowledge, which is available in the public domain, it is not the sheer number of photons absorbed into the links of DNA and RNA which effects and deactivates replication sequences. Disinfection can be achieved by using a short but high-energy pulse with 4 times less photons than the quantity present in light provided by a medium power continuous lamp (e.g. the CW type UV lamp used in the experiments).

Appropriate statistical sampling and counting were done. No exemptions were observed.

What is claimed is:

1. A method for remotely disinfecting liquids or gasses, comprising the steps of:
    distributing at least one optical fiber in a region where the liquids or gasses to be disinfected are presented;
    aligning a high intensity light source with said optical fiber; and
    radiating said liquid or gasses with light generated by said light source and transmitted by said optical fiber over a predetermined period of time;
    wherein said light is a laser which is converted from a primary radiation having a primary frequency into a secondary radiation having a secondary frequency different from the primary frequency, so that the secondary radiation is emitted from said optical fiber for radiating said liquid or gasses.

2. The method according to claim 1, wherein the conversion of the primary frequency into the secondary frequency is harmonically generated.

3. The method according to claim 1, wherein said region is an interior of a chamber containing the liquids or gasses to be disinfected, and said distributing comprises integrating said optical fiber into at least a wall of the chamber.

4. The method according to claim 1, wherein said optical fiber comprises at least one side emitting optical fiber distributed in the region where the liquid or gasses to be disinfected are presented.

5. The method according to claim 1, wherein said optical fiber comprises at least one end glowing optical fiber distributed in the region where the liquid or gasses to be disinfected are presented.

6. The method according to claim 1, further comprising obtaining spectroscopic data in the disinfected region, and transferring, in real time, said spectroscopic data from the disinfected region to a remote location for feedback control of the disinfecting process.

7. The method according to claim 1, wherein said light source comprises a single wavelength monochromatic high intensity source of light.

8. The method according to claim 1, wherein said light source comprises a polychromatic high intensity source of light having a wavelength of from about 249 nm to about 2400 nm.

9. The method according to claim 1, wherein said light source comprises a pulsed high intensity source of light.

10. The method according to claim 9, wherein said at least one optical fiber includes at least one of single mode, multi mode, graded index, gradient index, and polarization maintaining fibers or bundles of fibers.

11. The method according to claim 1, wherein said light source comprises a continuous high intensity source of light.

12. The method according to claim 1, wherein said light source comprises a high intensity source of ultra violet light having a wavelength of from about 187 nm to about 400 nm.

13. The method according to claim 1, wherein said light source comprises a high intensity source of visible light having a wavelength of from about 400 nm to about 700 nm.

14. The method according to claim 1, wherein said light source comprises a high intensity source of IR light having a wavelength of from about 800 nm to about 2400 nm.

15. The method according to claim 1, wherein the secondary radiation emitted from said optical fiber is in the visible region of the spectrum which is suitable for disturbing the breeding cycle of cockroaches.

16. A device for disinfecting liquids or gasses, comprising:
    a chamber containing the liquids or gasses to be disinfected;
    a laser for generating high intensity light;
    at least one optical fiber coupled to said laser for receiving said light therein, and arranged to deliver said light to at least one of an interior of said chamber, a wall of said chamber, and an exterior in the vicinity of said chamber for radiating the liquids or gases contained in said chamber with said light; and
    at least one crystal interface is attached or integrated to said at least one optical fiber for harmonically converting a first wavelength of incoming said light to a second wavelength of outgoing said light, said second wavelength being shorter than said first wavelength.

17. The device according to claim 16, wherein the laser is a polychromatic or monochromatic source of light having wavelength of from 220 nm to about 2400 nm.

18. The device according to claim 17, wherein the laser is a polychromatic microwave excitation lamp.

19. The device according to claim 17, wherein the optical fiber is an end glowing fiber, and the optical fiber is dimensionally arranged for producing at least one region of constructive interference in the chamber.

20. The device according to claim 17, further comprising a holographic optical element for producing at least one region of constructive interference in the chamber.

21. The device according to claim 17, wherein the chamber has a filtration unit having at least one of porous screen, membrane, surface disk, capillaries, magnetic elements and compounds for removal of particulate materials from said liquids or gasses, and the optical fiber is integrated into the filtration unit.

22. The device according to claim 17, wherein the chamber is an algae reactor or a biological reactor having industrial photosynthesis capability.

23. The device according to claim 17, wherein the chamber is a medical dialysis apparatus.

24. The device according to claim 16, wherein the laser is selected from the group consisting of flash lamp, fiber laser, solid state laser, gas laser, and crystal laser.

25. The device according to claim 16, wherein said optical fiber is coupled to the laser via a vacuum flange or a collimating optical interface which allows delivery of optical energy of said light within a specific spectral distribution and a damage threshold of said optical fiber.

26. The device according to claim 16, further comprising a transparent or opaque sleeve enclosing said optical fiber.

27. The device according to claim 26, wherein the sleeve is formed integrated with said optical fiber.

28. The device according to claim 16, wherein said optical fiber is geometrically distributed in the chamber for producing at least one region of constructive interference therein.

29. The device according to claim 16, wherein said optical fiber comprises side emitting fibers, distributed geometrically in a spiral or zigzag pattern.

30. The device according to claim 16, wherein the optical fiber is at least partially folded back to form at least one section of parallel fiber paths.

31. The device according to claim 28, wherein said at least one constructive interference causes an ultra violet hologram to be formed in an entire inner space of the chamber.

32. The device according to claim 16, further comprising a reflective end cup affixed to a terminal end of the optical fiber for producing at least one region of constructive interference in the chamber.

33. The device according to claim 16, further comprising a reflective member disposed parallel to at least one radiating section of said distributed optical fiber from which said light escapes to radiate said liquids or gasses.

34. The device according to claim 33, wherein the optical fiber is a side emitting fiber and the reflective member is an integral part of the side emitting fiber.

35. The device according to claim 16, wherein said optical fiber comprises at least one side emitting optical fiber.

36. The device according to claim 16, wherein said optical fiber comprises at least one end glowing optical fiber.

37. The device according to claim 16, further comprising a supporting member for supporting said optical fiber within the chamber.

38. The device according to claim 16, wherein the chamber is a sewage pipe.

39. The device according to claim 16, wherein the chamber is selected from the group consisting of an aeration volume of loosely packed soil, a cabinet, a closet, the space below a raised floor, the space above a lowered ceiling, the space in a hollow wall, an attic, a crawl space, the space between stored articles, the space between infrastructure support connections, a water carrying pipe, a shoe, a modular attachment of a vacuum cleaner, a space in the head of a tooth brush, a space in the head of a brush, a space in a headphone's housing, a window frame, a water pond, a fridge, and a door frame.

40. The device according to claim 16, further comprising a computer system for controlling the output of the laser.

41. The device according to claim 16, further comprising at least an optical link for transferring real time spectroscopic data from the disinfected chamber to a computer system.

42. The device according to claim 16, wherein the crystal interface is a non linear crystal capable of generating at least one of 2nd, 3rd, and 4th harmonies of a primary frequency of said light generated by the laser.

43. The device according to claim 16, wherein the light generated by the laser is in the IR region of the spectrum, and said at least one crystal interface is configured to convert IR radiation into at least one of visible and UV radiation.

44. The device according to claim 16, wherein said at least one optical fiber is connected to at least two elastic diffusive tips, and said tips are grouped together to form a brush substantially extending into the liquids or gases to be disinfected.

45. The device according to claim 16, wherein walls of the chamber are transparent to said light which radiates the liquids or gases contained in the chamber from outside.

46. A method of installing interactive optical infrastructure and using the same for disinfecting liquids or gases, said method comprising the steps of:

distributing, in a conduit or a chamber containing the liquids or gasses to be disinfected, at least one optical fiber having a receptive first end termination, and a second end extending into the conduit or chamber, said second end being inter-mated at a predetermined angle to at least one modular 2nd, and/or 3rd, and/or 4th harmonic generation crystal module interface, wherein the crystal module interface is terminated with an isolating transparent lens facing the liquids or gasses to be disinfected;

aligning at least one high intensity light source with said optical fiber;

coupling, either directly or through a receptive vacuum interface, high intensity light generated by said light source into said first end termination of said optical fiber, said high intensity light having a primary wavelength in at least one of the visible, NIR, IR and UV regions of the electromagnetic spectrum;

illuminating or irradiating the liquids or gasses over a predetermined period of time with said high intensity light after said light has been harmonically generated, or converted to have a secondary wavelength in at least one of the UVA, UVB, UVC, visible, and IR regions of the electromagnetic spectrum.

47. A device for disinfecting liquids or gasses, comprising:

a chamber containing the liquids or gasses to be disinfected;

at least one of a solar collector and a concentrator harnessing global solar radiation for producing polychromatic or monochromatic light having a wavelength of from 220 nm to about 2400 nm;

at least one optical fiber coupled to said laser for receiving said light therein, and arranged to deliver said light to at least one of an interior of said chamber, a wall of said chamber, and an exterior in the vicinity of said chamber for radiating the liquids or gases contained in said chamber with said light; and at least one crystal interface is attached or integrated to said at least one optical fiber as an end termination thereof, for harmonically converting a first wavelength of incoming said light to a second wavelength of outgoing said light, said second wavelength being shorter than said first wavelength.

* * * * *